United States Patent [19]

Komoriya et al.

[11] Patent Number: 5,605,809
[45] Date of Patent: Feb. 25, 1997

[54] COMPOSITIONS FOR THE DETECTION OF PROTEASES IN BIOLOGICAL SAMPLES AND METHODS OF USE THEREOF

[75] Inventors: Akira Komoriya; Beverly S. Packard, both of Rockville, Md.

[73] Assignee: Oncoimmunin, Inc., Rockville, Md.

[21] Appl. No.: 331,383

[22] Filed: Oct. 28, 1994

[51] Int. Cl.$^6$ .............................. C12Q 1/00; C12Q 1/37; G01N 33/00
[52] U.S. Cl. ................... 435/23; 435/4; 435/7.6; 435/7.72; 435/7.9; 435/18; 436/86; 436/89; 436/74; 436/800; 436/172; 530/300
[58] Field of Search .................. 435/23, 7.5, 7.6, 435/7.8, 7.9, 18, 4, 7.72; 436/518, 800, 86, 89, 74, 172; 530/300

[56] References Cited

U.S. PATENT DOCUMENTS

| | | | |
|---|---|---|---|
| 4,557,862 | 12/1985 | Mangel et al. | 435/23 |
| 4,648,893 | 3/1987 | Roux | 435/23 |
| 4,708,929 | 11/1987 | Henderson | 435/7.5 |
| 4,780,421 | 10/1988 | Kameda et al. | 436/518 |
| 4,897,444 | 1/1990 | Brynes et al. | 435/23 |
| 5,212,298 | 5/1993 | Rademacher et al. | 435/7.92 |

OTHER PUBLICATIONS

Carmel, A. et al. *FEBS Letters*, 30:11 (1973).
Knight, C. G. et al. *FEBS* 10610, 296:263 (1992).
Latt, S. A. et al. *Analytical Biochemistry* 50:56 (1972).
Matayoshi, E. D. et al. *Science*, 247: (1990).
Nagase, H. et al. *The Journal of Biological Chemistry* 269:20952 (1994).
Wang, G. T. et al. *Tetrahedron Letters* 31:6493 (1990).
Wu, P. et al. *Analytical Biochemistry* 218:1 (1994).

Primary Examiner—Gary E. Hollinden
Assistant Examiner—Louise Leary
Attorney, Agent, or Firm—Townsend and Townsend and Crew LLP

[57] ABSTRACT

The present invention provides for novel reagents whose fluorescence increases in the presence of particular proteases. The reagents comprise a characteristically folded peptide backbone each end of which is conjugated to a fluorophore. When the folded peptide is cleaved, as by digestion with a protease, the fluorophores provide a high intensity fluorescent signal at a visible wavelength. Because of their high fluorescence signal in the visible wavelengths, these protease indicators are particularly well suited for detection of protease activity in biological samples, in particular in frozen tissue sections. Thus this invention also provides for methods of detecting protease activity in situ in frozen sections.

33 Claims, 5 Drawing Sheets

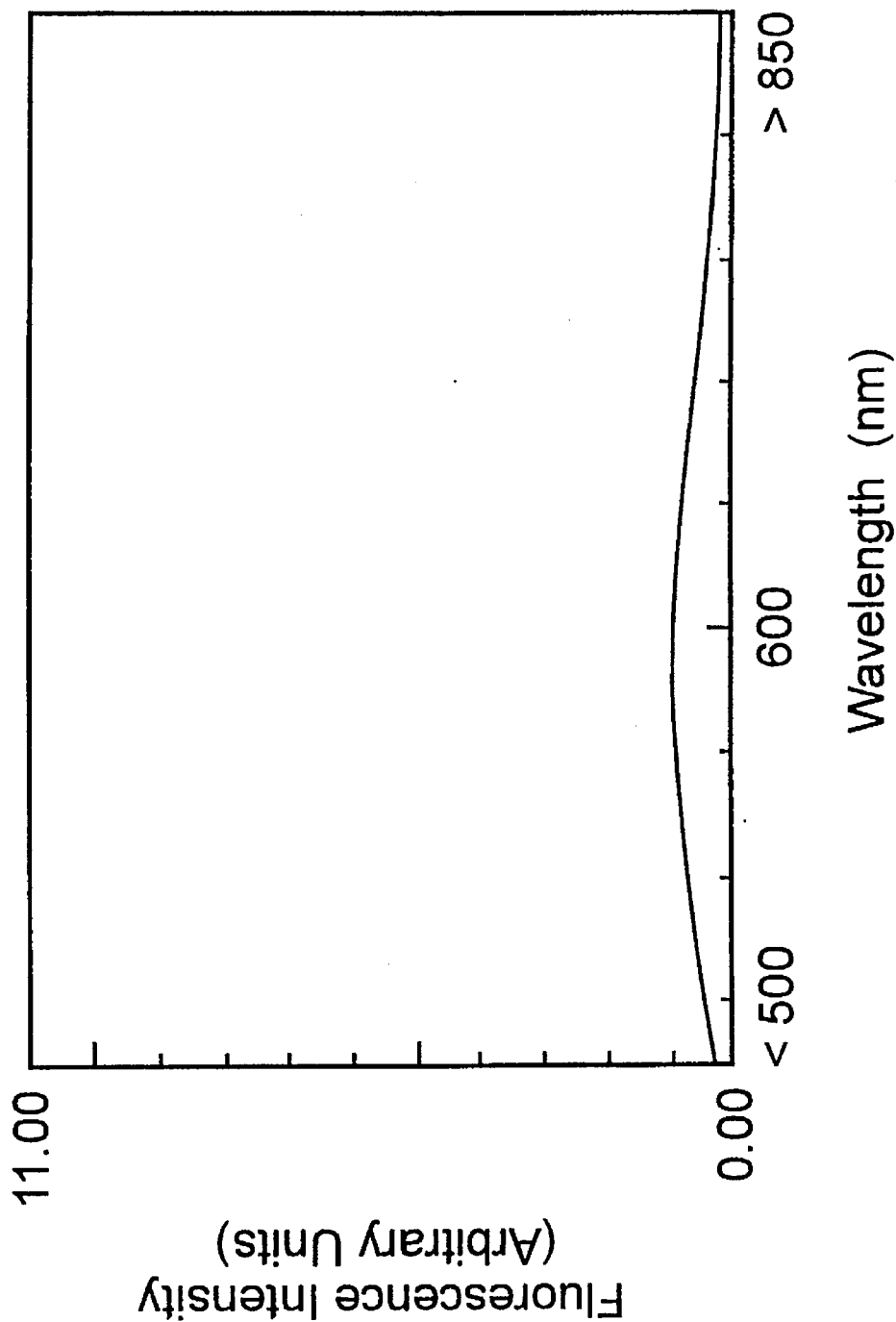

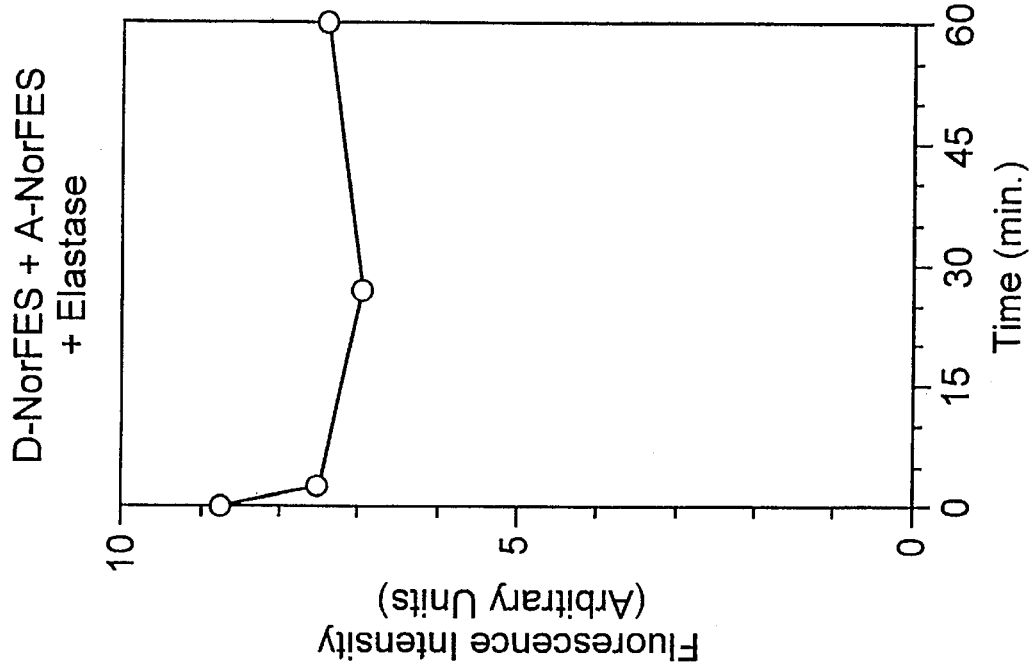
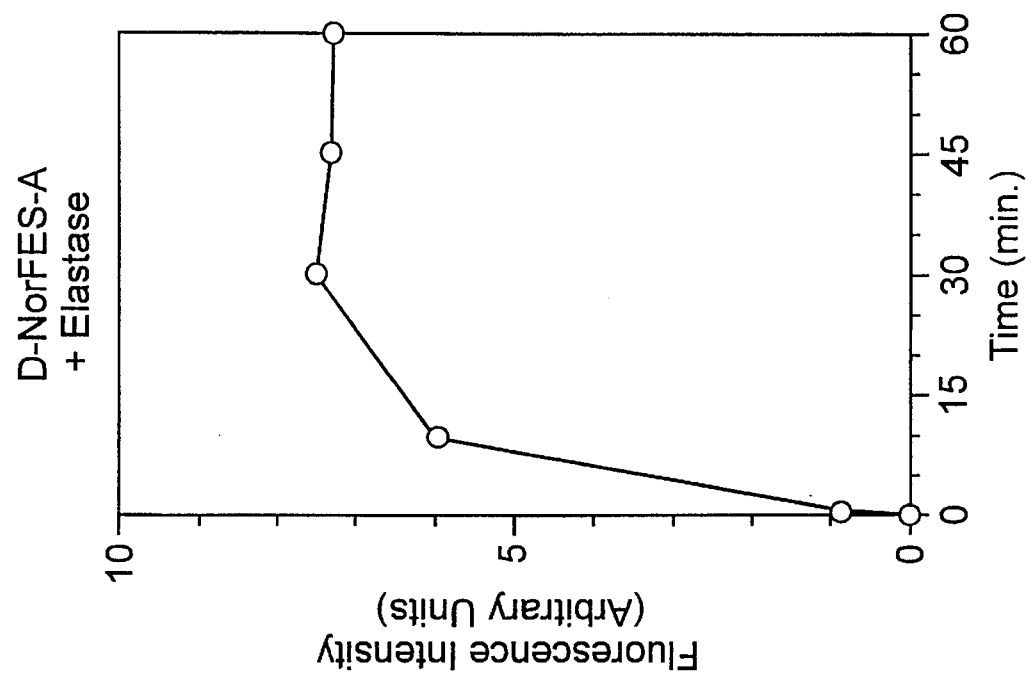

COMPOSITIONS FOR THE DETECTION OF PROTEASES IN BIOLOGICAL SAMPLES AND METHODS OF USE THEREOF

FIELD OF THE INVENTION

This invention pertains to a class of novel fluorogenic compositions whose fluorescence level increases in the presence active proteases. These fluorogenic protease indicators typically fluoresce at visible wavelengths and are thus highly useful for the detection and localization of protease activity in biological samples.

BACKGROUND OF THE INVENTION

Proteases represent a number of families of proteolytic enzymes that catalytically hydrolyze peptide bonds. Principal groups of proteases include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, *Textbook of Biochemistry with Clinical Correlations*, John Wiley and Sons, Inc. N.Y. (1993)).

Similarly, proteases have been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. *Adv. Cancer. Res.*, 44: 139 (1985).

Clearly measurement of changes in the activity of specific proteases is clinically significant in the treatment and management of the underlying disease states. Proteases, however, are not easy to assay. Typical approaches include ELISA using antibodies that bind the protease or RIA using various labeled substrates. With their natural substrates assays are difficult to perform and expensive. With currently available synthetic substrates the assays are expensive, insensitive and nonselective. In addition, many "indicator" substrates require high quantifies of protease which results, in part, in the self destruction of the protease.

Recent approaches to protease detection rely on a cleavage-induced spectroscopic change in a departing chromogen or fluorogen located in the P1' position (the amino acid position on the carboxyl side of the cleavable peptide bond) (see, for example U.S. Pat. Nos. 4,557,862 and 4,648,893). However, many proteases require two or three amino acid residues on either side of the scissile bond for recognition of the protease and thus, these approaches lack protease specificity.

Recently however, fluorogenic indicator compositions have been developed in which a "donor" fluorophore is joined to an "acceptor" chromophore by a short bridge containing a (7 amino acid) peptide that is the binding site for an HIV protease and linkers joining the fluorophore and chromophore to the peptide (Wang et al. *Tetra. Letts.* 45: 6493–6496 (1990)). The signal of the donor fluorophore was quenched by the acceptor chromophore through a process of resonance energy transfer. Cleavage of the peptide resulted in separation of the chromophore and fluorophore, removal of the quench and a subsequent signal from the fluorophore.

Unfortunately, the design of the bridge between the donor and the acceptor led to relatively inefficient quenching limiting the sensitivity of the assay. In addition, the chromophore absorbed light in the ultraviolet range reducing the sensitivity for detection in biological samples which typically contain molecules that absorb strongly in the ultraviolet.

Clearly fluorogenic protease indicators that show a high signal level when cleaved, and a very low signal level when intact, that show a high degree of protease specificity, and that operate exclusively in the visible range thereby rendering them suitable for use in biological samples are desirable. The compositions of the present invention provide these and other benefits.

SUMMARY OF THE INVENTION

The present invention provides for novel reagents whose fluorescence increases in the presence of particular proteases. These fluorogenic protease indicators provide a high intensity fluorescent signal at a visible wavelength when they are digested by a protease. Because of their high fluorescence signal in the visible wavelengths, these protease indicators are particularly well suited for detection of protease activity in biological samples, in particular, in frozen tissue sections.

The fluorogenic protease indicators of the present invention are compositions suitable for detection of the activity of a protease. These compositions have the general formula:

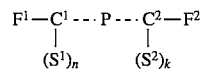

in which P is a peptide comprising a protease binding site consisting of about 2 to about 8, more preferably about 2 to about 6 and most preferably about 2 to about 4 amino acids; $F^1$ and $F^2$ are fluorophores; $S^1$ and $S^2$ are peptide spacers ranging in length from 1 to about 50 amino acids; n and k are independently 0 or 1; and $C^1$ and $C^2$ are conformation determining regions comprising peptides ranging in length from about 1 to about 3 amino acids. The conformation determining regions each introduce a bend into the composition thereby creating a generally U-shaped configuration of the composition in which the fluorophores are adjacent to each other with a separation of less than about 100 Å. When either of the spacers ($S^1$ and $S^2$) are present they are linked to the protease binding site by a peptide bond to the alpha carbon of the terminal amino acid. Thus, when n is 1, $S^1$ is joined to $C^1$ by a peptide bond through a terminal alpha amino group of $C^1$, and when k is 1, S: is joined to $C^2$ by a peptide bond through a terminal alpha carboxyl group of $C^2$.

In a preferred embodiment, protease binding site (P) is a tetrapeptide, $C^1$ is a tripepride and $C^2$ is an amino acid or a dipeptide. The composition thus has the formula:

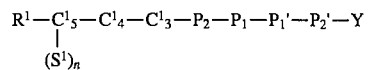

where $C^1_5$, $C^1_4$, $C^1_3$, $P_2$, $P_1$, $P_1'$, $P_2'$ are amino acids, and Y is a composition selected from the group consisting of compounds of formulas:

$$C^2_3 - C^2_4 \cdots F^2 \atop | \atop (S^2)_k \qquad \text{III}$$

and $$C^2_3 \cdots F^2 \atop | \atop (S^2)_k \qquad \text{IV}$$

where $C^2_3$, $C^2_3$ are amino acids.

In a particularly preferred embodiment, the composition is a composition of formula II in which the amino acid composition of P corresponds to the 4 amino acids symmetrically disposed adjacent to the cleavage site (the $P_1$-$P_1'$ peptide bond) cut by a particular protease. The conformation determining regions ($C^1$ and $C^2$) then comprise the remaining residues of the protease binding site regions. Some of these $C^1$ and $C^2$ amino acids, however, may be substituted according to one or more of the following guidelines:

1. If the $P_2'$ site is not a proline then $C^2$ is a dipeptide (Formula III) Pro-Cys or Aib-Cys, while conversely, if the $P_2'$ site is a proline then $C^2$ is a single amino acid residue (Formula IV) Cys.
2. If the $P_2$ site is not a proline then $C^1$ is a tripeptide consisting of Asp-$C^1_4$-Pro, Asp-$C^1_4$-Aib, Asp-Aib-Pro, Asp-Pro-$C^1_3$, Asp-Pro-Aib, or Asp-Aib-Aib, while if the $P_2$ site is a proline residue then group $C^1$ is a tripeptide consisting of Asp-$C^1_4$-$C^1_3$ or Asp-$C^1_4$-Aib.
3. If the $P_3$ residue is a proline then $C^1$ is a tripeptide consisting of Asp-$C^1_4$-Pro or Asp-Aib-Pro.
4. If the $P_4$ residue is a proline then $C^1$ is a tripeptide consisting of Asp-Pro-$C^1_3$ or Asp-Pro-Aib.
5. If $P_2$ and $C^1_3$ are both not prolines then $C^1$ is a tripeptide consisting of Asp-Pro-$C^1_3$, Asp-Aib-$C^1_3$, Asp-$C^1_4$-Pro, Asp-$C^1_4$-Aib, Asp-Pro-Aib, or Asp-Aib-Pro.

Table 2 indicates particularly preferred protease binding sites (P) and suitable conformation determining regions ($C^1$ and $C^2$). Thus, this invention also includes compositions of formula II in which $P_2$ is Pro, Gly, Phe, Arg, Leu, Gln, Glu, Ile, or Ala; $P_1$ is Cys, Met, Nle, Arg, Leu, Gly, His, Glu, Ala, or Asn; $P_1'$ is Thr, Ser, Met, Nle, Leu, Ala, Ile, Phe, Val, Glu, or Tyr; and $P_2'$ is Ile, Gly, Met, Nle, Leu, Ala, Gln, Arg, Val or Asn. Particularly preferred are compositions of formula II in which the P domain ($P_2$-$P_1$-$P_1'$-$P_2'$) is Pro-Met-Ser-Ile, Pro-Nle-Ser-Ile, Gly-Arg-Thr-Gly, Arg-Met-Ser-Leu, Arg-Nle-Ser-Leu, Gly-Arg-Ser-Leu, Leu-Leu-Ala-Leu, Leu-Gly-Ile-Ala, Gln-Gly-Ile-Leu, Gln-Gly-Leu-Leu, Gln-Gly-Ile-Ala, Gln-Ala-Ile-Ala, Glu-Gly-Leu-Arg, Gly-His-Phe-Arg, Leu-Glu-Val-Met, Leu-Glu-Val-Nle, Ile-His-Ile-Gln, Ala-Asn-Tyr-Asn, Ala-Gly-Glu-Arg, or Ala-Gly-Phe-Ala, Gln-Gly-Leu-Ala, Ala-Gln-Phe-Val, Ala-Gly-Val-Glu, Phe-Cys-Met-Leu, Phe-Cys-Nle-Leu (Sequence ID Nos. 1–25, respectively).

This invention also includes compositions of formula II in which $C^1_5$ is Asp; $C^1_4$ is Ala, Met, Nle, Aib, Pro, Ile, Gly, Asp or Arg; and $C^1_3$ is Ile, Aib or Pro. Particularly preferred are compositions in which the $C^1$ conformation determining region ($C^1_5$-$C^1_4$-$C^1_3$) is Asp-Ala-Ile, Asp-Ile-Pro, Asp-Aib-Pro, Asp-Gly-Pro, Asp-Asp-Pro, Asp-Arg-Pro, Asp-Ile-Aib, Asp-Aib-Aib, Asp-Gly-Aib, Asp-Asp-Aib or Asp-Arg-Aib.

Preferred protease indicators include compositions of formula II in which $P_2'$ is a Pro, in which case $C^2$ is a single amino acid. Thus Y is formula IV in which $C^2_3$ is preferably a Cys. In another embodiment, Y is formula III and $C^2_3$ is Pro and $C^2_4$ is Cys.

In a particularly preferred embodiment $F^1$ is a fluorophore having an excitation wavelength ranging from 315 nm to about 650 nm, $F^2$ is a fluorophore having an excitation wavelength ranging from 315 nm to about 650 nm or both $F^1$ and $F^2$ are fluorophores having excitation and absorbtion wavelengths ranging from 315 nm to about 650 nm. $F^1$ may be the donor fluorophore with $F^2$ the acceptor fluorophore, or conversely, $F^2$ may be the donor fluorophore with $F^1$ the acceptor fluorophore. $F^1$ may be 5-carboxytetramethyl-rhodamine or 7-hydroxy-4-methylcoumarin-3-acetic acid, while $F^2$ may be rhodamine X acetamide or 7-diethylamino-3-((4'-iodoacetyl)amino)phenyl)-4-methylcoumarin.

In a particularly preferred embodiment, n and k are 0; $C^1$ is Asp-Ala-Ile; P is Pro-Nle-Ser-Ile; $C^2$ is Pro-Cys; $F^1$ is 5-carboxytetramethylrhodamine; and $F^2$ is rhodamine X acetamide. In another particularly preferred embodiment, n and k are 0; $C^1$ is Asp-Ala-Ile; P is Pro-Met-Ser-Ile; $C^2$ is Pro-Cys; $F^1$ is 5-carboxytetramethylrhodamine; and $F^2$ is rhodamine X acetamide.

This invention also includes compositions in which $C^1$ is Asp-Ala-Ile; P is Pro-Met-Ser-Ile or Pro-Nle-Ser-Ile; $C^2$ is Pro-Cys; and either n or k is 1 and either $S^1$ or $S^2$ is a spacer having the sequence Asp-Gly-Ser-Gly-Gly-Gly-Glu-Lys, Lys-Glu-Asp-Gly-Gly-Asp-Lys, Asp-Gly-Ser-Gly-Glu-Asp-Glu-Lys, Asp-Gly-Gly-Gly-Lys-Lys, or Lys-Glu-Asp-Glu-Gly-Ser-Gly-Asp-Lys. In these compositions $F^1$ may be 5'-carboxytetramethylrhodamine; and $F^2$ may be rhodamine X acetamide. These compositions may be conjugated to a solid support or to a lipid including membrane lipids or liposomes.

In another embodiment, any of the compositions described above may be used in a method for detecting protease activity in a sample (Sequence ID Nos. 26–30 respectively). The sample may be a sample of "stock" protease, such as is used in research or industry, or it may be a biological sample. Thus, this invention provides for a method of detecting protease activity in a sample by contacting the sample with any of the compositions described above and then detecting a change in fluorescence of the fluorogenic composition where an increase in fluorescence indicates protease activity. The sample is preferably a biological sample which may include biological fluids such as sputum or blood, tissue samples such as biopsies or sections, and cell samples either as biopsies or in culture. Particularly preferred are tissue sections, such as frozen sections, that have not been embedded or fixed.

BRIEF DESCRIPTION OF THE DRAWINGS

(FIG. 1A: HPLC before the addition of elastase showing the late eluting peak representing the intact indicator molecule. FIG. 1B HPLC after the addition of elastase with detection at 550 nm where both fluorophores absorb. FIG. 1C HPLC after the addition of elastase with detection at 580 nm where $F^2$ absorbs maximally.

FIGS. 2A and 2B show the emission spectra of the D-NorFES-A fluorogenic protease indicator after (FIG. 2B) before and after the addition of elastase.

FIGS. 4A and 4B show the fluorescence intensity of the donor fluorophore as a function of time after addition of 1 unit of elastase. FIG. 4A The fluorogenic protease indicator of FIG. 1. FIG. 4B The peptide backbone of the fluorogenic protease of FIG. 1 singly labeled with each of the two fluorophores. D-NorFES-A is the $F^1$-Asp-Ala-Ile-Pro-Nle-Ser-Ile-Pro-Cys-$F^2$ protease indicator where $F^1$ is a donor fluorophore (5'-carboxytetramethylrhodamine (C2211) and $F^2$ is an acceptor fluorophore (rhodamine X acetamide (R492). D-NorFES and A-NorFES each designate a molecule having the same peptide backbone, but bearing only one of the two fluorophores.

DESCRIPTION OF THE PREFERRED EMBODIMENT

Definitions

Figure 1A:
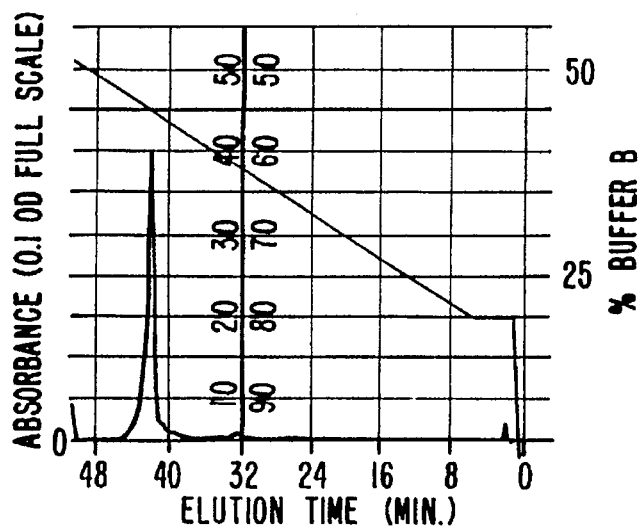
FIGS. 1A, 1B, and 1C show an HPLC analysis of the D-NorFES-A protease indicator ($F^1$-Asp-Ala-Ile-Pro-Nle-Ser-Ile-Pro-Cys-$F^2$ (Sequence ID No. 31) protease indicator where $F^1$ is a donor fluorophore (5'-carboxytetramethylrhodamine (C2211) and $F^2$ is an acceptor fluorophore (rhodamine X acetamide (R492))) before and after the addition of elastase.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "protease binding site" is used herein to refers to an amino acid sequence that is characteristically recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A fluorophore is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore which absorbs, but does not characteristically re-emit light.

"Peptides" and "polypeptides" are chains of amino acids whose α carbons are linked through peptide bonds formed by a condensation reaction between the α carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include peptide mimetics such as amino acids joined by an ether as opposed to an amide bond.

The polypeptides described herein are written with the amino terminus at the left and the carboxyl terminus at the right. The amino acids comprising the peptide components of this invention are numbered with respect to the protease cleavage site, with numbers increasing consecutively with distance in both the carboxyl and amino direction from the cleavage site. Residues on the carboxyl site are either notated with a "'" as in $P_1'$, or with a letter and superscript indicating the region in which they are located. The "'" indicates that residues are located on the carboxyl side of the cleavage site.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" or "region" refers to a characteristic region of a polypeptide. The domain may be characterized by a particular structural feature such as a β turn, an alpha helix, or a β pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The terms "protease activity" or "activity of a protease" refer to the cleavage of a peptide by a protease. Protease activity comprises the "digestion" of one or more peptides into a larger number of smaller peptide fragments. Protease activity of particular proteases may result in hydrolysis at particular peptide binding sites characteristically recognized by a particular protease. The particular protease may be characterized by the production of peptide fragments bearing particular terminal amino acid residues.

The amino acids referred to herein are described by shorthand designations as follows:

TABLE 1

Amino acid nomenclature.
Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| α-aminoisobutyric acid | Aib | |

Fluorogenic Indicators of Protease Activity

This invention provides for novel fluorogenic molecules useful for detecting protease activity in a sample. The fluorogenic protease indicators of the present invention generally comprise a fluorophore (donor) linked to an "acceptor" molecule by a peptide having an amino acid sequence that is recognized and cleaved by a particular protease. The donor fluorophore typically is excited by incident radiation at a particular wavelength which it then re-emits at a different (longer) wavelength. When the donor fluorophore is held in close proximity to the acceptor molecule, the acceptor absorbs the light re-emitted by the fluorophore thereby quenching the fluorescence signal of the donor molecule. Cleavage of the peptide joining the donor fluorophore and the acceptor results in separation of the two molecules, release of the quenching effect and increase in fluorescence.

In one basic application, the fluorogenic molecules of this invention may be used to assay the activity of purified protease made up as a reagent (e.g. in a buffer solution) for experimental or industrial use. Like many other enzymes, proteases may loose activity over time, especially when they are stored as their active forms. In addition, many proteases exist naturally in an inactive precursor form (e.g. a zymogen) which itself must be activated by hydrolysis of a particular peptide bond to produce the active form of the enzyme prior to use. Because the degree of activation is variable and because proteases may loose activity over time, it is often desirable to verify that the protease is active and to often quantify the activity before using a particular protease in a particular application.

Previous approaches to verifying or quantifying protease activity involve combining an aliquot of the protease with its substrate, allowing a period of time for digestion to occur and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, the fluorogenic reagents of this invention and the subsequent change in fluorescence is monitored (e.g., using a fluorimeter).

In addition to determining protease activity in "reagent" solutions, the fluorogenic compositions of the present invention may be utilized to detect protease activity in biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Previously described fluorogenic protease indicators typically absorb light in the ultraviolet range (e.g., Wang et at., supra. ). They are thus unsuitable for sensitive detection of protease activity in biological samples which typically contain constituents (e.g., proteins) that absorb in the ultraviolet range. In contrast, the fluorescent indicators of the present invention both absorb and emit in the visible range (400 nm to about 700 nm). These signals are therefore not readily quenched by, nor is activation of the fluorophores, that is absorbtion of light, interfered with by background molecules; therefore they are easily detected in biological samples.

In addition, unlike previous fluorogenic protease indicators which often utilize a fluorophore and a quenching chromophore, the indicators of the present invention may utilize two fluorophores (i.e. fluorophore as both donor and acceptor). Pairs of fluorophores may be selected that show a much higher degree of quenching than previously described chromophore/fluorophore combinations. In fact, previous compositions have been limited to relatively low efficiency fluorophores because of the small degree of quenching obtainable with the matching chromophore ( Wang et al. supra.). In contrast, the fluorogenic protease indicators of this invention utilize high efficiency fluorophores and are able to achieve a high degree of quenching while providing a strong signal when the quench is released by cleavage of the peptide substrate. The high signal allows detection of very low levels of protease activity. Thus the fluorogenic protease indicators of this invention are particularly well suited for in situ detection of protease activity.

The fluorogenic protease indicators of the present have the general formula:

where P is a peptide comprising a protease binding site, $F^1$ and $F^2$ are fluorophores, $C^1$ and $C^2$ are conformation determining regions, and $S^1$ and $S^2$ are optional peptide spacers. $F^1$ may be the donor fluorophore while $F^2$ is the acceptor fluorophore, or conversely, $F^2$ may be the donor fluorophore while $F^1$ is the acceptor fluorophore. The protease binding site provides an amino acid sequence (a peptide) that is recognized and cleaved by the protease whose activity the indicator is designed to reveal. The protease binding site is typically a straight chain peptide ranging in length from about 2 to about 8, more preferably from about 2 to about 6 and most preferably 2 to about 4 amino acids in length.

The conformation determining region is an amino acid sequence that introduces a bend into the molecule. The combined effect of the two conformation determining regions is to put two bends into the peptide backbone of the composition so that it achieves a substantially U-shaped conformation. This U-shaped conformation brings the fluorophores attached to the amino and carboxyl termini of $C^1$ and $C^2$ respectively into closer proximity to each other. The fluorophores are thus preferably positioned adjacent to each other at a distance less than about 100 angstroms. The fluorophores ($F^1$ and $F^2$) are typically conjugated directly to the conformation determining regions, although they may be joined by linkers. The optional spacers ($S^1$ and $S^2$) when present, are used to link the composition to a solid support.

The substantially U-shaped conformation increases the protease specificity of the composition. The amino acid sequences comprising the conformation determining regions (the arms of the U) are less accessible to the enzyme due to steric hinderance with each other and with the attached fluorophores. The protease binding site (presented on the bottom portion of the U) is relatively unobstructed by either the fluorophore or the complementarity determining region and is thus readily accessible to the protease.

Protease Binding Site and Conformation Determining Regions

The protease binding site and conformation determining regions form a contiguous amino acid sequence (peptide). The protease binding site is an amino acid sequence that is recognized and cleaved by a particular protease. It is well known that various proteases cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine.

A particular protease, however, will not cleave every bond in a protein that has the correct adjacent amino acid. Rather, the proteases are specific to particular amino acid sequences which serve as recognition domains for each particular protease.

Any amino acid sequence that comprises a recognition domain and can thus be recognized and cleaved by a protease is suitable for the "protease binding site" of the fluorogenic protease indicator compositions of this invention. Known protease substrate sequences and peptide inhibitors of proteases posses amino acid sequences that are recognized by the specific protease they are cleaved by or that they inhibit. Thus known substrate and inhibitor sequences provide the basic sequences suitable for use in the protease recognition region. A number of protease substrates and inhibitor sequences suitable for use as protease binding domains in the compositions of this invention are indicated in Table 2. One of skill will appreciate that this is not a complete list and that other protease substrates or inhibitor sequences may be used.

The amino acid residues comprising the protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

$$P_2\text{-}P_1\text{-}P_1'\text{-}P_2'$$

and the protease would cleave the binding region between $P_1$ and $P_1'$.

In a preferred embodiment, the protease binding region of the fluorogenic protease indicators of the present invention is selected to be symmetric about the cleavage site. Thus, for example, where a binding region is Ile-Pro-Met-Ser-ILe (e.g. α-1 anti-trypsin, Sequence ID No. 32) and the cleavage occurs between Met and Ser then a 4 amino acid residue binding region based on this sequence would be:

$$\begin{array}{cccc} P_2 & P_1 & P_1' & P_2' \\ -\text{Pro}- & \text{Met}- & \text{Ser}- & \text{ILe}- \end{array}$$

Other examples of binding domains selected out of longer sequences are provided in Table 2. The remaining amino or carboxyl residues that are not within the protease binding domain may remain as part of the conformation determining regions subject to certain limitations as will be explained below. Thus, in the instant example, the amino terminal Ile may be incorporated into the $C^1$ conformation determining region.

Various amino acid substitutions may be made to the amino acids comprising the protease binding domain to increase binding specificity, to eliminate reactive side chains, or to increase rigidity (decrease degrees of freedom) of the molecule. Thus, for example, it is often desirable to substitute methionine (Met) residues, which bear a oxidizable sulfur, with norleucine. Thus, in the example given, a preferred protease binding region will have the sequence:

$$\begin{array}{cccc} P_2 & P_1 & P_1' & P_2' \\ -\text{Pro}- & \text{Nle}- & \text{Ser}- & \text{ILe}- \end{array}$$

Conformation Determining Regions

Conformation determining regions ($C^1$ and $C^2$) are peptide regions on either end of the protease cleavage region that both stiffen and introduce bends into the peptide backbone of the fluorogenic protease indicator molecules of this invention. The combination of the two conformation determining regions and the relatively straight protease cleavage region produces a roughly U-shaped molecule with the cleavage site at the base (middle) of the "U".

Amino acids such as proline (Pro) and α-aminobutyric acid (Aib) are selected both to introduce bends into the peptide molecule and to increase the rigidity of the peptide backbone. The $C^1$ and $C^2$ domains are selected such that the "arms" of the U are rigid and the attached fluorophores are localized adjacent to each other at a separation of less than about 100 angstroms. In order to maintain the requisite stiffness of the peptide backbone and placement of the fluorophores, the conformation determining regions are preferably 4 amino acids in length or less, or alternatively are greater than about 18 amino acids in length and form a stable alpha helix conformation or a β-pleated sheet.

In a preferred embodiment, the peptide backbone of the fluorogenic protease indicators of the present invention will comprise a tripeptide $C^1$ region, a tetrapeptide P region and a single amino acid or dipeptide $C^2$ region. These compounds may be represented by the formula:

$$R^1-C^1{}_5-C^1{}_4-C^1{}_3-P_2-P_1-P_1'-P_2'-Y \qquad \text{II}$$
$$\mid$$
$$(S^1)_n$$

where Y is either $$\begin{array}{c} C^2{}_3-C^2{}_4\text{---}F^2 \\ \mid \\ (S^2)_k \end{array} \qquad \text{III}$$

or $$\begin{array}{c} C^2{}_3\text{---}F^2 \\ \mid \\ (S^2)_k \end{array} \qquad \text{IV}$$

In these formulas the peptide binding region is designated $-P_2\text{-}P_1\text{-}P_1'\text{-}P_2'-$, while the amino acid residues of conformation determining regions $C^1$ and $C^2$ are designated $-C^1{}_5\text{-}C^1{}_4\text{-}C^1{}_3\text{-}$ and $-C^2{}_3\text{-}C^2{}_4\text{-}$ respectively. The $C^2$ region may either be an amino acid or a dipeptide. Whether the $C^2$ region is a dipeptide or an amino acid, the $F^2$ fluorophore and the $L^2$ spacer, when present, are always coupled to the carboxyl terminal residue of $C^2$. When a spacer is present on the $C^2$ region, it is attached the carboxyl terminal residue of $C^2$ by a peptide bond to the α carboxyl group.

As indicated above, the conformation determining regions typically contain amino acid residues such as a proline (Pro) that introduce a bend into the molecule and increase its stiffness. One of skill in the art will appreciate, however that where the terminal residues of the protease binding region (P) are themselves bend-creating residues such as proline, it is not necessary to locate a bend-creating residue at the position closest to P in the C region attached to that terminus. The conformation determining regions are thus designed by first determining the protease binding region, as described above, determining the "left-over" residues that would lie in the conformation determining regions, and if necessary, modifying those residues according to the following guidelines:

1. If the $P_2'$ site is not a proline then $C^2$ is a dipeptide (Formula III) Pro-Cys or Aib-Cys, while conversely, if the $P_2'$ site is a proline then $C^2$ is an amino acid residue (Formula IV) Cys.

2. If the $P_2$ site is not a proline then $C^1$ is a tripeptide consisting of Asp-$C^1_4$-Pro, Asp-$C^1_4$-Aib, Asp-Aib-Pro, Asp-Pro-$C^1_3$, Asp-Pro-Aib, or Asp-Aib-Aib, while if the $P_2$ site is a proline residue then group $C^1$ is a tripeptide consisting of Asp-$C^1_4$-$C^1_3$ or Aib-$C^1_4$-$C^1_3$.

3. If the $P_3$ residue is a proline then $C^1$ is a tripride consisting of Asp-$C^1_4$-Pro or Asp-Aib-Pro.

4. If the $P_4$ residue is a proline then $C^1$ is a tripride consisting of Asp-Pro-$C^1_3$ or Asp-Pro-Aib.

5. If $P_2$ and $C^1_3$ are both not prolines then $C^1$ is a tripeptide consisting of Asp-Pro-$C^1_3$, Asp-Aib-$C^1_3$, Asp-$C^1_4$-Pro, Asp-$C^1_4$-Aib, Asp-Pro-Aib, or Asp-Aib-Pro.

As indicated above, any methionine (Met) may be replaced with a norleucine (Nle). A number of suitable peptide backbones consisting of $C^1$, P and $C^2$ are provided in Table 2.

TABLE 2

Illustration of the design of the conformation determining regions and protease binding site based on known protease substrate and inhibitor sequences. Italics indicate residues that are added to create a bend and to increase rigidity of the conformatin determining regions. Normal font indicates residues of the substrate or inhibitor that forms the protease binding site. Brackets indicate residues that must are preferably replaced. The thick line indicates the location at which the protease binding site is cleaved.

| Substrate/Inhibitor | CDR ($C^1$) | | | Protease Binding Site (P) | | | | CDR ($C^2$) | | Seq ID |
|---|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ | |
| α-1 anti-trypsin | *Asp* | Ala | Ile | Pro | Met Nle | Ser | Ile | *Pro Aib* | Cys | 35 |
| plasminogen activator inhibitor 2 | *Asp* | Met *Aib Pro* | (Thr) *Aib Pro* | Gly | Arg | Thr | Gly | *Pro Aib* | Cys | 36 |
| neutrophil leukocyte elastase inhibitor | *Asp* | Ala *Aib* | (Thr) *Aib Pro* | Phe | Cys | Met Nle | Leu | *Pro Aib* | Cys | 37 |
| anti-plasmin inhibitor | *Asp* | Aib | (Ser) *Aib Pro* | Arg | Met Nle | Ser | Leu | *Pro Aib* | Cys | 38 |
| anti-α-1 thrombin | *Asp* | Ile *Aib* | (Ala) *Aib Pro* | Gly | Arg | Ser | Leu | *Pro Aib* | Cys | 39 |
| α-1 antichymotrypsin | *Asp* | Aib | (Thr) *Aib Pro* | Leu | Leu | Ser | Leu | *Pro Aib* | Cys | 40 |
| interstitial type III (human liver) collagen | *Asp* | Gly *Aib* | Pro *Aib* | Leu | Gly | Ile | Ala | *Pro Aib* | Cys | 41 |
| type I collagen for collagenase Bovine α 1 | *Asp* | Gly *Aib Pro* | Pro *Aib* | Gln | Gly | Ile | Leu | *Pro Aib* | Cys | 42 |
| type I collagen chick α2 | *Asp* | Gly *Aib Pro* | Pro *Aib* | Gln | Gly | Leu | Leu | *Pro Aib* | Cys | 43 |
| human α1 type II collagen | *Asp* | Gly *Aib Pro* | Pro *Aib* | Gln | Gly | Ile | Ala | *Pro Aib* | Cys | 44 |
| type III collagen - AIA | *Asp* | Gly *Aib Pro* | Pro *Aib* | Gln | Ala | Ile | Ala | *Pro Aib* | Cys | 45 |
| type III collagen (human skin) | *Asp* | Gly *Aib Pro* | Pro *Aib* | Gln | Gly | Ile | Ala | *Pro Aib* | Cys | 55 |
| human α 2 macroglobulin | *Asp* | Gly *Aib Pro* | Pro *Aib* | Glu | Gly | Leu | Arg | *Pro Aib* | Cys | 46 |
| stromelysin cleavage sites of stromelysin-1d | *Asp* | Asp *Aib Pro* | (Val) *Aib Pro* | Gly | His | Phe | Arg | *Pro Aib* | Cys | 47 |
| stromelysin cleavage sites of stromelysin-1 | *Asp* | Asp *Aib Pro* | (Thr) *Aib Pro* | Leu | Glu | Val | Met Nle | *Pro Aib* | Cys | 48 |
| stromelysin cleavage site of proteoglycan link protein | *Asp* | Arg *Aib Pro* | (Ala) *Aib Pro* | Ile | His | Ile | Gln | *Pro Aib* | Cys | 49 |
| gelatinase type IV collagenase site of 72 K gelatinases | *Asp* | Asp *Aib Pro* | (Val) *Aib Pro* | Ala | Asn | Tyr | Asn | *Pro Aib* | Cys | 56 |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. Brackets indicate residues that must are preferably replaced. The thick line indicates the location at which the protease binding site is cleaved.

| Substrate/Inhibitor | CDR ($C^1$) | | | Protease Binding Site (P) | | | | CDR ($C^2$) | | Seq ID |
|---|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ | |
| gelatinase type IV cleavage of gelatin | *Asp* | Gly *Aib Pro* | Pro *Aib* | Ala | Gly | Glu | Arg | Pro *Aib* | Cys | 50 |
| gelatinase type IV cleavage of gelatin | *Asp* | Gly *Aib Pro* | Pro *Aib* | Ala | Gly | Phe | Ala | Pro *Aib* | Cys | 51 |
| type III collagen (human skin) | *Asp* | Gly *Aib Pro* | Pro *Aib* | Gln | Gly | Leu | Ala | Pro *Aib* | Cys | 52 |
| Human FIB-CL propeptide | *Asp* | Asp *Aib Pro* | (Val) *Aib Pro* | Ala | Gln | Phe | Val | Pro *Aib* | Cys | 53 |
| Gelatin α1 (type 1) | *Asp* | Gly *Aib Pro* | Pro *Aib* | Ala | Gly | Val | Gln | Pro *Aib* | Cys | 54 |

"Donor" and "Acceptor" Fluorophores

A fluorophore excited by incident radiation absorbs light and then subsequently re-emits that light at a different (longer) wavelength. However, in the presence of a second class of molecules, known as "acceptors" the light emitted by a so-called donor fluorophore is absorbed by the acceptor thereby quenching the fluorescence signal of the donor. Thus, use of two fluorophores, as opposed to a fluorophore/ chomophore pair, allows a clearer assessment of the overlap between the emission spectrum of the donor and the excitation spectrum of the acceptor. This facilitates the design of a peptide backbone that allows allowing optimization of the quenching. This results in a high efficiency donor/acceptor pair facilitating the detection of low concentrations of protease activity. Thus, although a fluorophore/chromophore combination may be suitable, in a preferred embodiment, the fluorogenic protease inhibitors of this invention will comprise two fluorophores.

The "donor" and "acceptor" molecules are typically selected as a matched pair such that the absorption spectra of the acceptor molecule overlaps the emission spectrum of the donor molecule as much as possible. In addition, the donor and acceptor fluorophores are preferably selected such that both the absorbtion and the emission spectrum of the donor molecule is in the visible range (400 nm to about 700 nm). The fluorophores thereby provide a signal that is detectable in a biological sample thus facilitating the detection of protease activity in biological fluids, tissue homogenates, in situ in tissue sections, and the like. The emission spectra, absorption spectra and chemical composition of many fluorophores are well known to those of skill in the art (see, for example, *Handbook of Fluorescent Probes and Research Chemicals,* R. P. Haugland, ed. which is incorporated herein by reference).

Preferred fluorophore pairs include the rhodamine derivatives. Thus, for example 5-carboxytetramethylrhodamine (C2211 available from Molecular Probes, Eugene, Wash., U.S.A.) (Formula V) is a particularly preferred donor molecule and

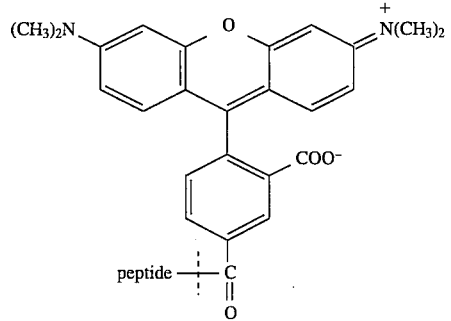

rhodamine X acetamide (R492 from Molecular Probes) (Formula VI) is a particularly preferred receptor molecule. These fluorophores are particularly preferred since the

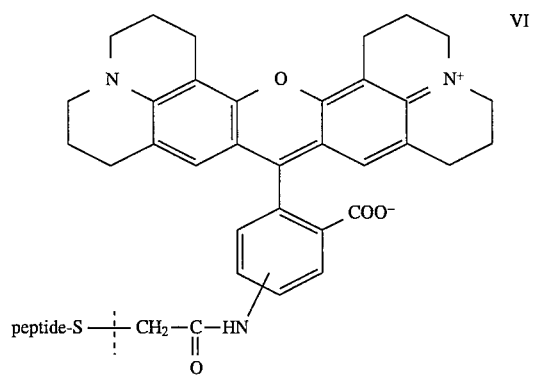

excitation and emission of both members of this donor/ acceptor pair are in the visible wavelengths, the molecules have high extinction coefficients and the molecules have high fluorescence yields in solution. The extinction coefficient is a measure of the light absorbance at a particular wavelength by the chromophore and is therefore related to its ability to quench a signal, while the fluorescence yield is the ratio of light absorbed to light re-emitted and is a measure of the efficiency of the fluorophore and thus effects the sensitivity of the protease indicator.

Of course, while not most preferred, fluorophores that absorb and emit in the ultraviolet may also be used in the protease indicators of the present invention. One particularly preferred ultraviolet absorbing pair of fluorophores is 7-hydroxy-4-methylcoumarin-3-acetic acid as the donor molecule (Formula VII)

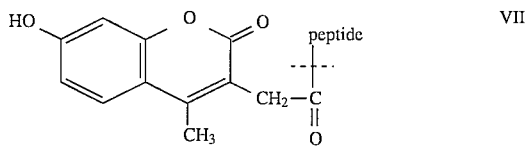

and 7-diethylamino-3-((4'-iodoacetyl)amino)phenyl)-4-methylcoumarin (Formula VIII) as the acceptor molecule.

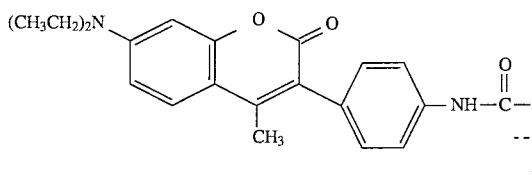

These and other fluorophores are commercially available from a large number of manufacturers such as Molecular Probes (Eugene, Oreg., U.S.A.).

Preparation of Fluorogenic Protease Indicators

The fluorogenic protease indicators of the present invention are preferably prepared by first synthesizing the peptide backbone, i.e. the protease cleavage site (P), the two conformation determining regions ($C^1$ and $C^2$), and the spacers ($S^1$ and $S^2$) if present. The fluorophores are then chemically conjugated to the peptide. The fluorophores are preferably conjugated directly to the peptide however, they may also be coupled to the peptide through a linker. Finally, where the fluorogenic protease indicator is to be bound to a solid support, it is then chemically conjugated to the solid support via the spacer ($S^1$ or $S^2$) either directly or through a linker.

a) Preparation of the Peptide Backbone

Solid phase peptide synthesis in which the C-terminal amino acid of the sequence is attached to an insoluble support followed by sequential addition of the remaining amino acids in the sequence is the preferred method for preparing the peptide backbone of the compounds of the present invention. Techniques for solid phase synthesis are described by Barany and Merrifield, *Solid-Phase Peptide Synthesis;* pp. 3–284 in *The Peptides: Analysis, Synthesis, Biology. Vol. 2: Special Methods in Peptide Synthesis, Part A.,* Merrifield, et al. *J. Am. Chem. Soc.* 85, 2149–2156 (1963), and Gross and Meienhofer, eds. Academic press, N.Y., 1980 and Stewart et al., *Solid Phase Peptide Synthesis,* 2nd ed. Pierce Chem. Co., Rockford, Ill. (1984) which are incorporated herein by reference. Solid phase synthesis is most easily accomplished with commercially available peptide synthesizers utilizing FMOC or TBOC chemistry. The chemical synthesis of the peptide component of a fluorogenic protease indicator is described in detail in Example 1.

Alternatively, the peptide components of the fluorogenic protease indicators of the present invention may be synthesized utilizing recombinant DNA technology. Briefly, a DNA molecule encoding the desired amino acid sequence is synthesized chemically by a variety of methods known to those of skill in the art including the solid phase phosphoramidite method described by Beaucage and Carruthers, *Tetra. Letts.* 22:1859–1862 (1981), the triester method according to Matteueci, et al., *J. Am. Chem. Soc.,* 103:3185 (1981), both incorporated herein by reference, or by other methods known to those of skill in the art. It is preferred that the DNA be synthesized using standard β-cyanoethyl phosphoramidites on a commercially available DNA synthesizer using standard protocols.

The oligonucleotides may be purified, if necessary, by techniques well known to those of skill in the art. Typical purification methods include, but are not limited to gel electrophoresis, anion exchange chromatography (e.g. Mono-Q column, Pharmacia-LKB, Piscataway, N.J., U.S.A.), or reverse phase high performance liquid chromatography (HPLC). Method of protein and peptide purification are well known to those of skill in the art. For a review of standard techniques see, *Methods in Enzymology Volume 182: Guide to Protein Purification,* M. Deutscher, ed. (1990), pages 619–626, which are incorporated herein by reference.

The oligonucleotides may be converted into double stranded DNA either by annealing with a complementary oligonucleotide or by polymerization with a DNA polymerase. The DNA may then be inserted into a vector under the control of a promoter and used to transform a host cell so that the cell expresses the encoded peptide sequence. Methods of cloning and expression of peptides are well known to those of skill in the art. See, for example, Sambrook, et al., *Molecular Cloning: A Laboratory Manual* (2nd Ed., Vols. 1–3, Cold Spring Harbor Laboratory (1989)), *Methods in Enzymology,* Vol. 152: *Guide to Molecular Cloning Techniques* (Berger and Kimmel (eds.), San Diego: Academic Press, Inc. (1987)), or *Current Protocols in Molecular Biology,* (Ausubel, et al. (eds.), Greene Publishing and Wiley-Interscience, New York (1987), which are incorporated herein by reference.

b) Linkage of the Fluorophores to the Peptide Backbone

The fluorophores are linked to the peptide backbone by any of a number of means well known to those of skill in the art. In a preferred embodiment, the fluorophore is linked directly from a reactive site on the fluorophore to a reactive group on the peptide such as a terminal amino or carboxyl group, or to a reactive group on an amino acid side chain such as a sulfur, an amino, or a carboxyl moiety. Many fluorophores normally contain suitable reactive sites. Alternatively, the fluorophores may be derivatized to provide reactive sites for linkage to another molecule. Fluorophores derivatized with functional groups for coupling-to a second molecule are commercially available from a variety of manufacturers. The derivatization may be by a simple substitution of a group on the fluorophore itself, or may be by conjugation to a linker. Various linkers are well known to those of skill in the art and are discussed below.

As indicated above, in a preferred embodiment, the fluorophores are directly linked to the peptide backbone of the protease indicator. Thus, for example, the 5'-carboxytetramethylrhodamine (C2211) fluorophore may be linked to aspartic acid via the alpha amino group of the amino acid as shown in Formula V. The iodoacetamide group of rhodamine X acetamide (R492)) may be linked by reaction with the sulfhydryl group of a cystein as indicated in formula VI. Means of performing such couplings are well known to those of skill in the art, and the details of one such coupling are provided in Example 1.

One of skill in the art will appreciate that when the peptide spacers ($S^1$ or $S^2$) are present (as is discussed below), the fluorophores are preferably linked to the conformation determining regions through a reactive group on the side chain of the terminal amino acid of $C^1$ or $C^2$ as the spacers themselves form a peptide linkage with the terminal amino and carboxyl groups of $C^1$ or $C^2$ respectively.

c) Selection of Spacer Peptides and Linkage to a Solid Support

The fluorogenic protease indicators of the present invention may be obtained in solution or linked to a solid support. A "solid support" refers to any solid material that does not dissolve in or react with any of the components present in the solutions utilized for assaying for protease activity using the fluorogenic protease indicator molecules of the present invention and that provides a functional group for attachment of the fluorogenic molecule. Solid support materials are well known to those of skill in the art and include, but are not limited to silica, controlled pore glass (CPG), polystyrene, polystyrene/latex, carboxyl modified teflon, dextran, derivatized polysaccharaides such as agar bearing amino, carboxyl or sulfhydryl groups, various plastics such as polyethylene, acrylic, and the like. Also of use are "semi-solid" supports such as lipid membranes as found in cells and in liposomes. One of skill will appreciate that the solid supports may be derivatized with functional groups (e.g. hydroxyls, amines, carboxyls, esters, and sulfhydryls) to provide reactive sites for the attachment of linkers or the direct attachment of the peptide.

The fluorogenic protease indicators may be linked to a solid support directly through the fluorophores or through the peptide backbone comprising the indicator. Linkage through the peptide backbone is most preferred.

When it is desired to link the indicator to a solid support through the peptide backbone, the peptide backbone may comprise an additional peptide spacer (designated $S^1$ or $S^2$ in Formula I). The spacer may be present at either the amino or carboxyl terminus of the peptide backbone and may vary from about 1 to about 50 amino acids, more preferably from 1 to about 20 and most preferably from 1 to about 10 amino acids in length. Particularly preferred spacers include Asp-Gly-Ser-Gly-Gly-Gly-Glu-Asp-Glu-Lys, Lys-Glu-Asp-Gly-Gly-Asp-Lys, Asp-Gly-Ser-Gly-Glu-Asp-Glu-Lys, and Lys-Glu-Asp-Glu-Gly-Ser-Gly-Asp-Lys.

The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine) having side chains to which a linker or the solid support itself, is easily coupled. Alternatively the linker or the solid support itself may be attached to the amino terminus of $S^1$ or the carboxyl terminus of $S^2$.

In a preferred embodiment, the peptide spacer is actually joined to the solid support by a linker. The term "linker", as used herein, refers to a molecule that may be used to link a peptide to another molecule, (e.g. a solid support, fluorophore, etc.). A linker is a hetero or homobifunctional molecule that provides a first reactive site capable of forming a covalent linkage with the peptide and a second reactive site capable of forming a covalent linkage with a reactive group on the solid support. The covalent linkage with the peptide (spacer) may be via either the terminal carboxyl or amino groups or with reactive groups on the amino acid side-chain (e.g. through a disulfide linkage to a cysteine).

Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine).

Particularly preferred linkers are capable of forming covalent bonds to amino groups, carboxyl groups, or sulfhydryl. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Finally, sulfhydryl-binding linkers include reactive groups such as sulfhydryl groups, acrylates, isothiocyanates, isocyanates and the like. Particularly preferred linkers include sulfoMBS (m-maleimidobenzoyl-N-hydroxysulfosuccinimide ester) for linking amino groups (e.g. an amino group found on a lysine residue in the peptide) with sulfhydryl groups found on the solid support, or vice versa, for linking sulfhydryl groups (e.g. found on a cysteine residue of the peptide) with amino groups found on the solid support. Other particularly preferred linkers include EDC (1-ethyl-3-(3-dimethylaminopropryl)-carbodiimide) and bis-(sulfosuccinimidyl suberate). Other suitable linkers are well known to those of skill in the art.

The fluorogenic compounds of the present invention may be linked to the solid support through either the $S^1$ or the $S^2$ spacer such that the donor fluorophore is either retained on the solid support after cleavage of the molecule by a protease or such that the donor fluorophore goes into solution after cleavage. In the former case, the substrate is then assayed for fluorescence to detect protease activity, while in the later case the solution is assayed for fluorescence to detect protease activity.

Detection of Protease Activity

The present invention also provides methods for utilizing the fluorogenic protease indicators to detect protease activity in a variety of contexts. Thus, in one embodiment, the present invention provides for a method of using the fluorogenic indicators to verify or quantify the protease activity of a stock solution of a protease used for experimental or industrial purposes. Verification of protease activity of stock protease solutions before use is generally recommended as proteases often to loose activity over time (e.g. through self-hydrolysis) or to show varying degrees of activation when activated from zymogen precursors.

Assaying for protease activity of a stock solution simply requires adding a quantity of the stock solution to a fluorogenic protease indicator of the present invention and measuring the subsequent increase in fluorescence. The stock solution and the fluorogenic indicator may also be combined and assayed in a "digestion buffer" that optimizes activity of the protease. Buffers suitable for assaying protease activity are well known to those of skill in the art. In general, a buffer will be selected whose pH corresponds to the pH optimum of the particular protease. For example, a buffer particularly suitable for assaying elastase activity consists of 50 mM sodium phosphate, 1 mM EDTA at pH 8.9. The measurement is most easily made in a fluorometer, and instrument that provides an "excitation" light source for the fluorophore and then measures the light subsequently emitted at a particular wavelength. Comparison with a control indicator solution lacking the protease provides a measure of the protease activity. The activity level may be precisely quantified by generating a standard curve for the protease/indicator combination in which the rate of change in fluorescence produced by protease solutions of known activity is determined.

While detection of the fluorogenic compounds is preferably accomplished using a fluorometer, detection may by a variety of other methods well known to those of skill in the art. Thus for example, since the fluorophores of the present invention emit in the visible wavelengths, detection may be simply by visual inspection of fluorescence in response to excitation by a light source. Detection may also be by means of an image analysis system utilizing a video camera interfaced to an digitizer or other image acquisition system. Detection may also be by visualization through a filter as under a fluorescence microscope. The microscope may just provide a signal that is visualized by the operator. However the signal may be recorded on photographic film or using a video analysis system. The signal may also simply be quantified in realtime using either an image analysis system or simply a photometer.

Thus, for example, a basic assay for protease activity of a sample will involve suspending or dissolving the sample in a buffer (at the pH optima of the particular protease being assayed), adding to the buffer one of the fluorogenic protease indicators of the present invention, and monitoring the resulting change in fluorescence using a spectrofluorometer. The spectrofluorometer will be set to excite the donor fluorophore at the excitation wavelength of the donor fluorophore and to detect the resulting fluorescence at the emission wavelength of the donor fluorophore.

In another embodiment, the protease activity indicators of the present invention may be utilized for detection of protease activity in biological samples. Thus, in a preferred embodiment, this invention provides for methods of detecting protease activity in isolated biological samples such as sputum, blood, blood cells, tumor biopsies, and the like, or in situ, in cells or tissues in culture, or in section where the section is unimbedded and unfixed.

a) Ex vivo Assays of Isolated Biological Samples

In one embodiment, the present invention provides for methods of detecting protease activity in an isolated biological sample. This may be determined by simply contacting the sample with a fluorogenic protease indicator of the present invention and monitoring the change in fluorescence of the indicator over time. The sample may be suspended in a "digestion buffer" as described above. The sample may also be cleared of cellular debris, e.g. by centrifugation before analysis.

Where the fluorogenic protease indicator is bound to a solid support the assay may involve contacting the solid support bearing the indicator to the sample solution. Where the indicator is joined to the solid support by the side of the molecule beating the donor fluorophore, the fluorescence of the support resulting from digestion of the indicator will then be monitored over time by any of the means described above. Conversely, where the acceptor molecule fluorophore is bound to a solid support, the test solution may be passed over the solid support and then the resulting luminescence of the test solution (due to the cleaved fluorophore) is measured. This latter approach may be particularly suitable for high throughput automated assays.

b) In situ Assays of Histological Sections

In another embodiment, this invention provides for a method of detecting in situ protease activity in histological sections. This method of detecting protease activity in tissues offers significant advantages over prior art methods (e.g. specific stains, antibody labels, etc.) because, unlike simple labeling approaches, in situ assays using the protease indicators indicate actual activity rather than simple presence or absence of the protease. Proteases are often present in tissues in their inactive precursor (zymogen) forms which are capable of binding protease labels. Thus traditional labeling approaches provide no information regarding the physiological state, visa vis protease activity, of the tissue.

The in situ assay method generally comprises providing a tissue section (preferably a frozen section), contacting the section with one of the fluorogenic protease indicators of the present invention, and visualizing the resulting fluorescence. Visualization is preferably accomplished utilizing a fluorescence microscope. The fluorescence microscope provides an "excitation" light source to induce fluorescence of the "donor" fluorophore. The microscope is typically equipped with filters to optimize detection of the resulting fluorescence. Thus, for example, for the fluorogenic protease indicators described in Example 1, a typical filter cube for a Nikon microscope would contain an excitation filter ($\lambda=510\pm12$ nm), a dichroic mirror ($\lambda=580$ nm) and an emission filter ($\lambda=580\pm10$ nm). As indicated above, the microscope may be equipped with a camera, photometer, or image acquisition system.

The sections are preferably cut as frozen sections as fixation or embedding will destroy protease activity in the sample.

The fluorogenic indicator may be introduced to the sections in a number of ways. For example, the fluorogenic protease indicator may be provided in a buffer solution, as described above, which is applied to the tissue section. Alternatively, the fluorogenic protease indicator may be provided as a semi-solid medium such as a gel or agar which is spread over the tissue sample. The gel helps to hold moisture in the sample while providing a signal in response to protease activity. The fluorogenic protease indicator may also be provided conjugated to a polymer such as a plastic film which may be used in procedures similar to the development of Western Blots. The plastic film is placed over the tissue sample on the slide and the fluorescence resulting from cleaved indicator molecules is viewed in the sample tissue under a microscope.

Typically the tissue sample must be incubated for a period of time to allow the endogenous proteases to cleave the fluorogenic protease indicators. Incubation times will range from about 10 to 60 minutes at 37° C.

c) In situ Assays of Cells in Culture

In yet another embodiment, this invention provides for a method of detecting in situ protease activity of cells in culture. The cultured cells are grown either on chamber slides or in suspension and then transferred to histology slides by cytocentrifugation. The slide is washed with phosphate buffered saline and coated with a semi-solid polymer or a solution containing the fluorogenic protease indicator. The slide is incubated at 37° C. for the time necessary for the endogenous proteases to cleave the protease indicator. The slide is then examined under a fluorescence microscope equipped with the appropriate filters as described above.

Protease Activity Detection Kits

The present invention also provides for kits for the detection of protease activity in samples. The kits comprise one or more containers containing the fluorogenic protease indicators of the present invention. The indicators may be provided in solution or bound to a solid support. Thus the kits may contain indicator solutions or indicator "dipsticks", blotters, culture media, and the like. The kits may also contain indicator cartridges (where the fluorogenic indicator is bound to the solid support by the "acceptor" fluorophore side) for use in automated protease activity detectors.

The kits additionally may include an instruction manual that teaches the method and describes use of the components of the kit. In addition, the kits may also include other reagents, buffers, various concentrations of protease inhibitors, stock proteases (for generation of standard curves, etc), culture media, disposable cuvettes and the like to aid the detection of protease activity utilizing the fluorogenic protease indicators of the present invention.

EXAMPLES

The invention is illustrated by the following examples. These examples are offered by way of illustration, not by way of limitation.

Example 1

Synthesis of Fluorogenic Molecule for Detecting Protease Activity a) Synthesis of the Peptide Backbone The amino acid sequences Asp-Ala-Ile-Pro-Nle-Ser-Ile-Pro-Cys (Sequence ID No. 31) (where $C^1$ is Asp-Ala-Ile, P is Pro-Nle-Ser-Ile (Sequence ID No. 2) and $C^2$ is Pro-Cys) and Asp-Ala-Ile-Pro-Met-Ser-Ile-Pro-Cys (Sequence ID No. 32) (where $C^1$ is Asp-Ala-Ile, P is Pro-Met-Ser-Ile (Sequence ID No. 1) and $C^2$ is Pro-Cys) were synthesized manually utilizing a t-Boc Cys-Pam resin and t-Boc chemistry using the protocol for a coupling cycle given below in Table 3. The synthesized peptides were deprotected by treatment with hydrofluoric acid for 60 minutes under anhydrous conditions at a temperature of 4° C.

TABLE 3

Reaction steps for one coupling cycle (addition of one amino acid) for the synthesis of the peptide backbone of the fluorogenic protease inhibitors.

| Step | Process | Time (min) | # Repeats |
|---|---|---|---|
| 1 | TFA/DCM Pre-wash 15 ml, 50% (v/v) or 35% (v/v) | 2.0 | 1 |
| 2 | TFA/DCM Main Wash 15 ml, 50% (v/v) or 35% (v/v) | 28.0 | 1 |
| 3 | DCM washes, 10 ml | <0.33 | 4 |
| 4 | DIEA/DCM, 10% (v/v), 10 ml | 2.0 | 1 |
| 5 | DIEA/DCM, 10% (v/v), 10 ml | 8.0 | 1 |
| 6 | DCM washes, 10 ml | <0.33 | 5 |
| 7 | Resin wash with NMP (or DMF) | <0.33 | 5 |
| 8 | 5-fold excess t-Boc-amino acid with HOBT and DIPC in NMP or DMF | 90 to 120 | 1 |
| 9 | DCM wash | <0.33 | 1 |
| 10 | MeOH wash | <0.33 | 1 |
| 11 | DCM washes | <0.33 | 2 |
| 12 | DIEA wash | <0.33 | 1 |
| 13 | DCM washes | <0.33 | 3 |
| 14 | Ninhydrin | 5.0 | 1 |
| 15 | 3-fold excess t-Boc-amino acid/DIPC/DCM | 30 | 1 |
| 16 | MeOH wash | <0.33 | 1 |
| 17 | DCM washes | <0.33 | 5 |
| 18 | Ninhydrin test | 5 | 1 |
| 19 | Go to step 1 to couple next amino acid | | |

Crude post-HF deprotected and cleaved peptides were purified by reverse phase HPLC using a preparative $C_{18}$ column (YMC, Inc., Chariestown, N.C., U.S.A.). The solvent system utilized was water and acetonitrile containing 0.1% (v/v) trifluoroacetic acid CFFA). HPLC was performed using the following gradient at a flow rate of 10 ml/minute:

TABLE 4

HPLC gradient for purification of the peptide backbone.

| Time (min) | % Solvent A ($H_2O$ with TFA (0.1%)) |
|---|---|
| 0 | 100 |
| 7 | 100 |
| 8 | 90 |
| 68 | 50 |
| 78 | 50 |

Purification of methionine-containing peptides required subjecting the peptide to reducing conditions, e.g., dithiothreitol (DTT) and heat, to reduce methionine oxide to methionine. This reductive treatment was carried out by dissolving the peptide in 150 mM sodium phosphate buffer with 1 mM DTT, pH 7.5 for 30 minutes at 60° to 80° C. The reduction could also have been carded out under a weak acidic pH with 0.03N HCL but would have required a longer heating time. The subsequently HPLC purified methionine containing peptides were found to oxidize upon sitting either in aqueous solution or lyophilized form. The oxidized peptides were found to be reducible repeating the above reducing condition.

b) Derivatization of the Peptide Backbone With the Fluorophore Molecules

The peptides were derivatized sequentially with donor and acceptor fluorophores. Specifically the donor fluorophore (5'-carboxytetramethylrhodamine (C2211), available from Molecular Probes, Inc. Eugene, Oreg., U.S.A.) was first covalently linked to the amino terminus of the peptide. The peptide and the probe, at a molar ratio of 3:1 peptide to probe, were dissolved in a minimal amount of solvent NMP (N-methyl pyrolidone), usually 20 to 60 ml. One molar equivalent of DIEA (diisopropyl ethyl amine) was also added to the reaction mixture. The reaction was then incubated at 37° C. with times ranging between 12 hours and 3 days. After two days an additional 1 molar equivalent of dye molecule was sometimes added. The derivatization reached nearly maximal yield by 3 days. The peptide bearing the single C2211 fluorophore was then HPLC purified as described below.

The second (acceptor) fluorophore (rhodamine X acetamide (R492)) was then coupled to the carboxyl cystein of the peptide by a linkage between the iodoacetamide group of the fluorophore and the sulfhydryl group of the terminal cystein. This coupling was accomplished as described above for the first fluorophore.

The complete fluorogenic protease indicator was then purified by HPLC using an analytical reverse phase $C_3$ columns (2 ml void volume) from Waters Associates Inc. (Milford, Mass., U.S.A.) using the gradient shown in Table 5 running at 1 ml/minute.

TABLE 5

HPLC gradient for purification of the peptide bearing fluorophores.

| Time (min) | % Solvent A ($H_2O$ with TFA (0.1%)) |
|---|---|
| 0 | 100 |
| 1 | 100 |
| 2 | 80 |
| 6 | 80 |
| 66 | 50 |

The slow reactivity of both the amino and sulfhydryl groups in coupling the fluorophores appeared to be a function of the folded structure of the peptide backbone which sterically hindered access to the peptide's reactive groups. Control experiments using irrelevant linear peptides showed considerably faster linking. The folded structure is also supported by the results reported in Examples 2 and 3. A computer energy minimization model of the peptide also indicated possible preference for the peptide to assume a folded structure rather than an open extended structure. This is due largely to the presence of the conformation determining regions containing the two proline residues.

Example 2

The Fluorogenic Protease Indicators Provide a Strong Signal When Digested

In order to demonstrate that the fluorogenic protease indicators of this invention are easily digested by a protease, the degree of cleavage was determined by assaying for the appearance of indicator cleavage products in the presence of a protease.

Approximately 1 microgram of protease indicator, having the formula $F^1$-Asp-Ala-Ile-Pro-Nle-Ser-Ile-Pro-Cys-$F^2$ where $F^1$ is a donor fluorophore (5'-carboxytetramethylrhodamine (C2211)) linked to aspartic acid via the alpha amino group and $F^2$ is an acceptor fluorophore (rhodamine X acetamide (R492)) linked via the sulfhydryl group of the cystein was dissolved in a buffer consisting of 50 mM sodium phosphate, 1 mM EDTA at pH 8.9. To this solution was added 1 unit of elastase. The solution was analyzed by HPLC before and about 30 minutes after the addition of elastase. The digestion was carded out at 37° C. The HPLC separated components were monitored at a wavelength of 550 nm which allowed detection of both the C2211 fluorophore the R492 fluorophore and at 580 nm which allowed detection of the R492 fluorophore.

Figure 1B:
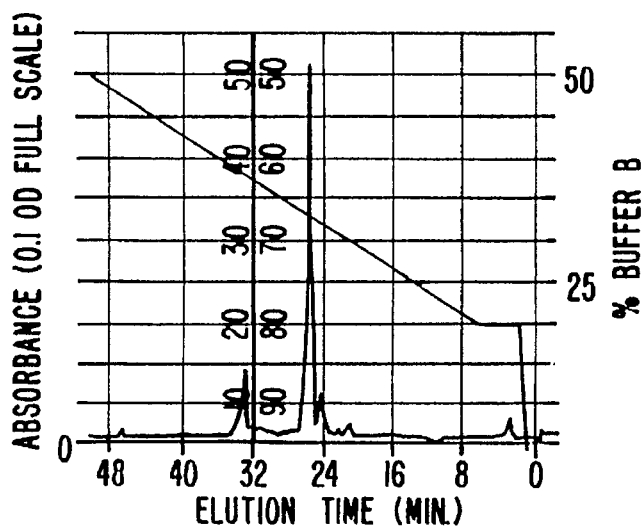
Figure 1C:
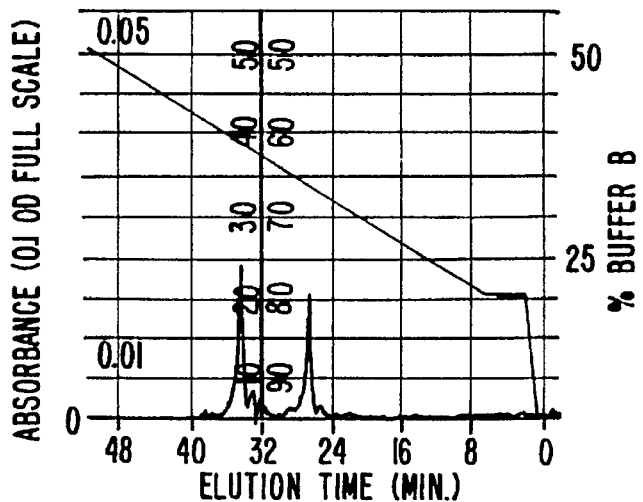

The results are indicated in FIG. 1 which shows the HPLC profiles of the fluorogenic protease indicator solution before and after addition of the protease elastase. FIG. 1(a) shows the HPLC before addition of the elastase showing a single peak representing the intact fluorogenic protease inhibitor. After addition of the elastase (FIGS. 1(b) and 1(c)) there was no trace of the late eluting single peak (FIG. 1(a)) indicating complete digestion of the fluorogenic protease indicator. In addition, the two predominant peaks in FIGS. 1(b) and 1(c) indicate that the digestion occurred primarily at a single site. There are a few smaller peaks indicating a low degree of digestion at other sites within the peptide sequence, however, the striking predominance of only two digestion peaks suggests that these secondary sites were not readily accessible to the elastase.

Changes in the emission spectrum of the fluorogenic protease indicator after the addition of an elastase protease was monitored using an SLM spectrofluorometer model 48000 with slit widths set at 4 nm on both the excitation and emission sides. All measurements were carded out at 37° C.

Figure 2B:
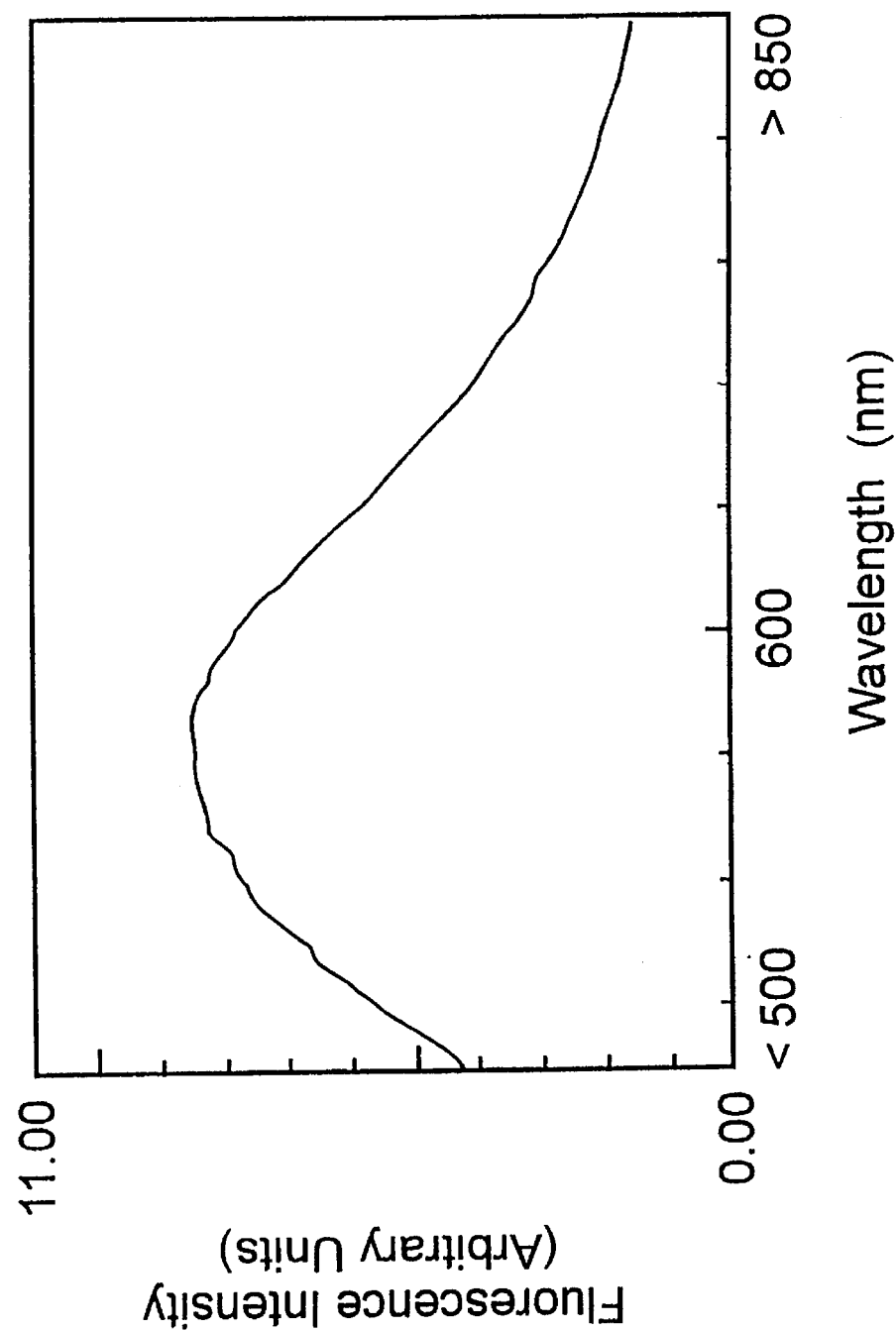
Figure 3:
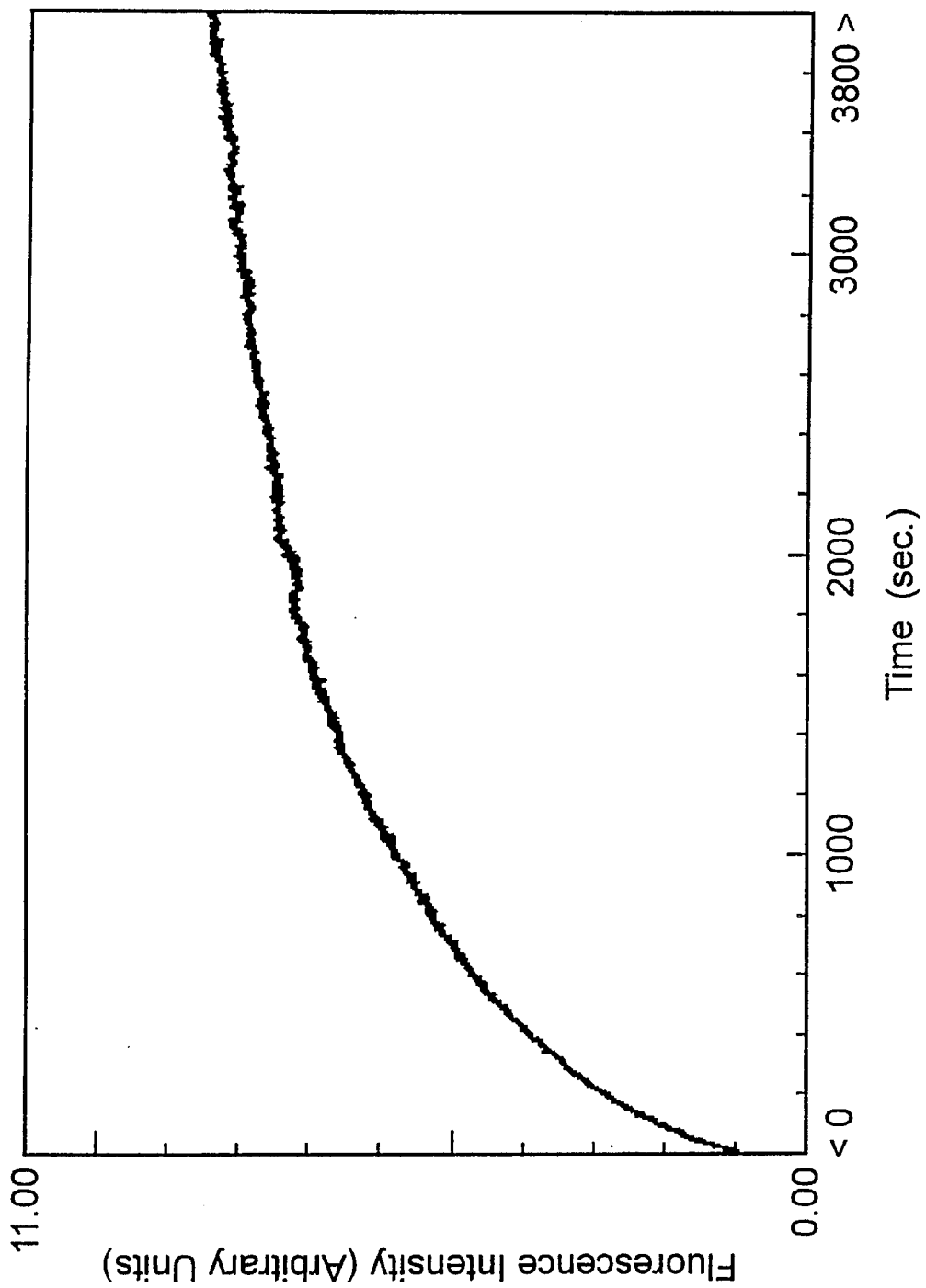
FIG. 3 shows the time-dependent increase of the fluorogenic protease indicator of FIG. 1, as a function of time after addition of 1 unit of elastase.

Spectra in FIG. 2 show emission of the fluorogenic protease indicator (a) before and (b) after addition of elastase, while the time dependent increase of the indicator's donor fluorophore emission intensity, after addition of elastase, is plotted in FIG. 3. The fluorogenic protease inhibitor showed more than a 10 fold increase in fluorescence at 589 nm after treatment with the elastase protease (FIG. 2(a) compared to FIG. 2(b)) with over a 5 fold increase in fluorescence occurring within the first 1000 seconds of exposure to the protease. The changes in intensity between treated and untreated indicators are, to some degree, a function of slit widths used, since they represent the signal integrated across the particular slit width. Thus, if wider slit widths were used (e.g. 8 or 16 nm slits) an even greater signal would be provided in response to digestion.

Example 3

The Fluorescence Signal Was Due to Intramolecular Energy Dequenching

In order to show that the fluorescence increase observed after protease treatment was due to intramolecular energy dequenching, the signal produced by elastase digestion of the fluorogenic protease indicator was compared to the signal produced by elastase treatment of the same peptide backbone coupled to either $F^1$ (C2211) or to $F^2$ (R492). The change in fluorescence intensity of the donor fluorophore after addition of 1 unit of elastase to equal concentrations of the double-fluorophore molecule and the two single-fluorophore molecules.

The results are illustrated in FIG. 4. The double-fluorophore molecule showed nearly complete quenching initially, followed by a dramatic increase in fluorescence after addition of the elastase which reached a constant value approximately 30 minutes after addition of the elastase (FIG. 4(a)). In contrast, the two single-fluorophore molecules showed virtually no initial quenching and no significant change in fluorescence after addition of the elastase. In fact, the fluorescence level was comparable to the fluorescence level of the fully digested double-fluorophore indicator molecule (FIG. 4(b)).

These results indicate that the increase in fluorescence intensity of the fluorogenic protease indicator is due to interruption of the resonance energy transferred intramolecularly from the donor fluorophore to the acceptor fluorophore and not to interaction between the fluorophore and the peptide backbone. This is significant since it is known that upon binding to a large protein or hydrophobic peptide the fluorescence of many hydrophobic fluorophores is quenched.

Example 4

Without being bound to a particular theory, it is believed that the fluorogenic protease indicators of the present invention achieve a high degree of protease specificity due to their folded structure, more particularly due to their relative rigid U-shaped conformation. The fluorescence obtained from the molecule reflects the average separation of two fluorophores. Thus, it was predicted that if the protease indicators existed in a relatively unfolded or flexible state, conditions that tend to cause unfolding (denaturation) would have little or no effect on the fluorescence of the molecule in the absence of a protease. Conversely, if the molecule is relatively rigid, then denaturing conditions would be expected to increase the fluorescence signal as the average separation of the fluorophores would be expected to increase thereby decreasing the quenching effect.

Thus, the effect of denaturing conditions on the fluorescence of the fluorogenic protease indicator in the absence of a protease was determined. First the change of fluorescence of the indicator of Example 1, as a function of temperature, was measured. Relative fluorescence intensity (of the donor fluorophore) increased approximately linearly from a value of about 0.6 (relative fluorescence units (RUs)) at 25°° C. to a value of about 1.2 RUs at 50° to 55° C. and thereafter reached a plateau.

Similarly when denatured with a chaotropic reagent (2M or 8M urea) the fluorescence intensity increase with time to a plateau as the molecule denatured (unfolded).

These data indicate that the fluorogenic protease indicator normally exists in a stable folded conformation created by the conformation determining regions, as was predicted by a model based on an energy minimization algorithm. The plateau fluorescence level represents residual quenching of the fluorophores still joined by the fully denatured peptide backbone. Digestion of the extended (denatured) peptide results in greater than a 2 fold increase in fluorescence as the fluorophores are able to move farther away from each other.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A fluorogenic composition for the detection of the activity of a protease, said composition having the formula:

$$F^1 - C^1_5 - C^1_4 - C^1_3 - P_2 - P_1 - P_1' - P_2' - Y \quad \quad II$$
$$\phantom{F^1 - C^1_5 - C^1_4 - C^1_3 - }|$$
$$\phantom{F^1 - C^1_5 - C^1_4 - C^1_3 - }(S^1)_n$$

wherein:

Y is a composition selected from the group consisting of compounds of formulas:

$$C^2_3 - C^2_4 - F^2 \quad \quad III$$
$$\phantom{C^2_3 - C^2_4 - }|$$
$$\phantom{C^2_3 - C^2_4 - }(S^2)_k$$

and $$C^2_3 - F^2 \quad \quad IV$$
$$|$$
$$(S^2)_k \quad ;$$

$C^1_5$, $C^1_4$, $C^1_3$, $P_2$, $P_1$, $P_1'$, $P_2'$, $C^2_3$, and $C^2_4$ are amino acids;

$P_2$-$P_1$-$P_1'$-$P_2'$ comprises a protease binding site;

$F^1$ and $F^2$ are fluorophores;

$S^1$ and $S^2$ are peptide spacers ranging in length from 1 to about 50 amino acids;

n and k are independently 0 or 1 and when n is 1, $S^1$ is joined to $C^1_5$ by a peptide bond through a terminal alpha amino group of $C^1$, and when k is 1, $S^2$ is joined to $C^{23}$ or to $C^2_4$ by a peptide bond through a terminal alpha carboxyl group of the respective $C^2_3$ or $C^2_4$; and wherein $C^1_5$-$C^1_4$-$C^1_3$ and $C^2_3$-$C^2_4$ or $C^2_3$ introduce a bend into the composition thereby creating a generally U-shaped configuration of said composition in which said fluorophores are adjacent to each other with a separation of less than about 100 Å.

2. The composition of claim 1, in which when $P_2'$ is not a proline then Y is formula III in which $C^2_3$-$C^2_4$ is Pro-Cys or α-aminoisobutyric acid (Aib)-Cys;

when $P_2'$ is a proline Y is formula IV in which $C^2_3$ is Cys;

when $P_2$ is a proline then $C^1_5$-$C^1_4$-$C^1_3$ is Asp-$C^1_4$-$C^1_3$, or Asp-$C^1_4$-Aib; and when $P_2$ is not a proline then $C^1_5$-$C^1_4$-$C^1_3$ is selected from the group consisting of Asp-$C^1_4$-Pro, Asp-$C^1_4$-Aib, Asp-Aib-Pro, Asp-Pro-$C^1_3$, Asp-Pro-Aib and Asp-Aib-Aib.

3. The composition of claim 2, wherein $P_2$ is selected from the group consisting of Pro, Gly, Phe, Arg, Leu, Gln, Glu, Ile, and Ala;

$P_1$ is selected from the group consisting of Cys, Met, norleucine (Nle), Gln, Arg, Leu, Gly, His, Glu, Ala, and Asn;

$P_1'$ is selected from the group consisting of Thr, Ser, Met, Nle, Leu, Ala, Ile, Phe, Vat, Glu, and Tyr; and $P_2'$ is selected from the group consisting of Ile, Gly, Met, Nle, Leu, Ala, Gln, Arg, Val and Asn.

4. The composition of claim 2, wherein $C^1_5$ is Asp;

$C^1_4$ is selected from the group consisting of Ala, Met, norleucine (Nle), α-aminoisobutyric acid (Aib), Pro, Ile, Gly, Asp and Arg; and $C^1_3$ is selected from the group consisting of Ile, Aib and Pro.

5. The composition of claim 2, wherein $P_2'$ is Pro;

Y is Formula IV;

$C^2_3$ is Cys.

6. The composition of claim 2, wherein

Y is Formula III;

$C^2_3$ is Pro; and $C^2_4$ is Cys.

7. The composition of claim 1, wherein $F^1$ is a fluorophore having an excitation wavelength ranging from 315 nm to about 650 nm.

8. The composition of claim 1, wherein $F^2$ is a fluorophore having an excitation wavelength ranging from 3 15 nm to about 650 nm.

9. The composition of claim 1, wherein $F^1$ is selected from the group consisting of 5-carboxytetramethyl-rhodamine and 7-hydroxy-4-methylcoumarin-3-acetic acid.

10. The composition of claim 1, wherein $F^2$ is selected from the group consisting of rhodamine X acetamide and 7-diethylamino-3-((4'-iodoacetyl)amino)phenyl)-4-methyl-coumarin.

11. The composition of claim 1, wherein n and k are 0;

$C^1_5$-$C^1_4$-$C^1_3$ is Asp-Ala-Ile;

$P_2$-$P_1$-$P_1'$-$P_2'$ is Pro-norleucine (Nle)-Ser-Ile;

$C^2_3$-$C^2_4$ is Pro-Cys;

$F^1$ is 5-carboxytetramethylrhodamine; and $F^2$ is rhodamine X acetamide.

12. The composition of claim 1, wherein n and k are 0;

$C^1_5$-$C^1_4$-$C^1_3$ is Asp-Ala-Ile;

$P_2$-$P_1$-$P_1'$-$P_2'$ is Pro-Met-Ser-Ile;

$C^2_3$-$C^2_4$ is Pro-Cys;

$F^1$ is 5-carboxytetramethylrhodamine; and $F^2$ is rhodamine X acetamide.

13. The composition of claim 1, wherein n is 1;

k is 0;

$S^1$ is Lys-Lys-Gly-Gly-Gly;

$C^1_5$-$C^1_4$-$C^1_3$ s Asp-Ala-Ile;

$P_2$-$P_1$-$P_1'$-$P_2'$ is Pro-norleucine (Nle)-Ser-Ile; and $C^2_3$-$C^2_4$ is Pro-Cys.

14. The composition of claim 13, wherein $S^1$ is conjugated to a solid support.

15. The composition of claim 1, wherein $C^1_5$-$C^1_4$-$C^1_3$ is Asp-Ala-Ile;

$P_2$-$P_1$-$P_1'$-$P_2'$ is Pro-norleucine (Nle)-Ser-Ile; and $C^2_3$-$C^2_4$ is Pro-Cys.

n is 0;

k is 1; and $S^2$ is Asp-Gly-Gly-Gly-Lys-Lys.

16. The composition of claim 15, wherein $S^2$ is conjugated to a solid support.

17. A method of detecting the activity of a protease in a biological sample, said method comprising the steps of:

contacting said biological sample with a fluorogenic composition having the formula:

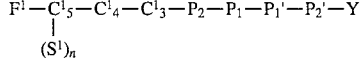

$$F^1-C^1_5-C^1_4-C^1_3-P_2-P_1-P_1'-P_2'-Y \quad\quad II$$
$$| $$
$$(S^1)_n$$

wherein:

Y is a composition selected from the group consisting of compounds of formulas:

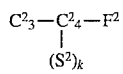

$$C^2_3-C^2_4-F^2 \quad\quad III$$
$$|$$
$$(S^2)_k$$

and

$$C^2_3-F^2 \quad\quad IV$$
$$|$$
$$(S^2)_k \quad ;$$

$C^1_5$, $C^1_4$, $C^1_3$, $P_2$, $P_1$, $P'_1$, $P'_2$, $C^2_3$, and $C^2_4$ are amino acids;

$P_2$-$P_1$-$P_1'$-$P_2'$ comprises a protease binding site;

$F^1$ and $F^2$ are fluorophores;

$S^1$ and $S^2$ are peptide spacers ranging in length from 1 to about 50 amino acids;

n and k are independently 0 or 1 and when n is 1, $S^1$ is joined to $C^1_5$ by a peptide bond through a terminal alpha amino group of $C^1$, and when k is 1, $S^2$ is joined to $C^2_3$ or to $C^2_4$ by a peptide bond through a terminal alpha carboxyl group of the respective $C^2_3$ or $C^2_4$; and wherein $C^1_5$-$C^1_4$-$C^1_3$ and $C^2_3$-$C^2_4$ or $C^2_3$ introduce a bend into the composition thereby creating a generally U-shaped configuration of said composition in which said fluorophores are adjacent to each other with a separation of less than about 100 Å; and detecting a change in fluorescence of said fluorogenic composition wherein an increase in fluorescence indicates protease activity.

18. The method of claim 17, wherein said biological sample is a histological section that has not been fixed or imbedded.

19. The method of claim 17, in which when $P_2'$ is not a proline then Y is formula III in which $C^2_3$-$C^2_4$ is Pro-Cys or α-aminoisobutyric acid (Aib)-Cys;

when $P_2'$ is a proline Y is formula IV in which $C^2_3$ is Cys;

when $P_2$ is a proline then $C^1_5$-$C^1_4$-$C^1_3$ is Asp-$C^1_4$-$C^1_3$, or Asp-$C^1_4$-Aib; and when $P_2$ is not a proline then $C^1_5$-$C^1_4$-$C^1_3$ is selected from the group consisting of Asp-$C^1_4$-Pro, Asp-$C^1_4$-Aib, Asp-Aib-Pro, Asp-Pro-$C^1_3$, Asp-Pro-Aib and Asp-Aib-Aib.

20. The method of claim 19, wherein $P_2$ is selected from the group consisting of Pro, Gly, Phe, Arg, Leu, Gln, Glu, Ile, and Ala;

$P_1$ is selected from the group consisting of Cys, Met, norleucine (Nle), Gln, Arg, Leu, Gly, His, Glu, Ala, and Asn;

$P_1'$ is selected from the group consisting of Thr, Ser, Met, Nle, Leu, Ala, Ile, Phe, Val, Glu, and Tyr; and $P_2'$ is selected from the group consisting of Ile, Gly, Met, Nle, Leu, Ala, Gln, Arg, Val and Asn.

21. The method of claim 20, wherein $C^1_5$ is Asp;

$C^1_4$ is selected from the group consisting of Ala, Met, norleucine (Nle), α-aminoisobutyric acid (Aib), Pro, Ile, Gly, Asp and Arg; and $C^1_3$ is selected from the group consisting of Ile, Aib and Pro.

22. The method of claim 20, wherein $P_2'$ is Pro;

Y is Formula IV;

$C^2_3$ is Cys.

23. The method of claim 20, wherein

Y is Formula III;

$C^2_3$ is Pro; and $C^2_4$ is Cys.

24. The method of claim 17, wherein $F^1$ is a fluorophore having an excitation wavelength ranging from about 315 nm to about 650 nm.

25. The method of claim 17, wherein $F^2$ is a fluorophore having an excitation wavelength ranging from about 315 nm to about 650 nm.

26. The method of claim 17, wherein $F^1$ is selected from the group consisting of 5-carboxytetramethylrhodamine and 7-hydroxy-4-methylcoumarin-3-acetic acid.

27. The method of claim 17, wherein $F^2$ is selected from the group consisting of rhodamine X acetamide and 7-diethylamino-3-((4'-iodoacetyl)amino)phenyl)-4-methylcoumarin.

28. The method of claim 17, wherein n and k are 0;

$C^1_5$-$C^1_4$-$C^1_3$ is Asp-Ala-Ile;

$P_2$-$P_1$-$P_1'$-$P_2'$ is Pro-Nle-Ser-Ile;

$C^2_3$-$C^2_4$ is Pro-Cys;

$F^1$ is 5-carboxytetramethylrhodamine; and $F^2$ is rhodamine X acetamide.

29. The method of claim 17, wherein n and k are 0;

$C^1_5$-$C^1_4$-$C^1_3$ is Asp-Ala-Ile;

$P_2$-$P_1$-$P_1'$-$P_2'$ is Pro-Met-Ser-Ile;

$C^2_3$-$C^2_4$ is Pro-Cys;

$F^1$ is 5-carboxytetramethylrhodamine; and $F^2$ is rhodamine X acetamide.

30. The method of claim 17, wherein n is 1;

k is 0;

$S^1$ is Lys-Lys-Gly-Gly-Gly;

$C^1_5$-$C^1_4$-$C^1_3$ is Asp-Ala-Ile;

$P_2$-$P_1$-$P_1'$-$P_2'$ is Pro-Nle-Ser-Ile; and $C^2_3$-$C^2_4$ is Pro-Cys.

31. The method of claim 30, wherein $S^1$ is conjugated to a solid support.

32. The method of claim 17, wherein $C^1_5$-$C^1_4$-$C^1_3$ is Asp-Ala-Ile;

$P_2$-$P_1$-$P_1'$-$P_2'$ is Pro-Nle-Ser-Ile; and $C^2_3$-$C^2_4$ is Pro-Cys.

n is 0;

k is 1; and $S^2$ is Asp-Gly-Gly-Gly-Lys-Lys.

33. The method of claim 32, wherein $S^2$ is conjugated to a solid support.

* * * * *

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Pro Met Ser Ile
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(2)
( D ) OTHER INFORMATION: /note= "Xaa is norleucine."

( x i ) SEQUENCE DESCRIPTION: SEQ ID NO:2:

Pro Xaa Ser Ile
1

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Gly Arg Thr Gly
1

( 2 ) INFORMATION FOR SEQ ID NO:4:

( i ) SEQUENCE CHARACTERISTICS:
( A ) LENGTH: 4 amino acids
( B ) TYPE: amino acid
( C ) STRANDEDNESS: single
( D ) TOPOLOGY: linear (ii) MOLECULE TYPE: peptide (xi) SEQUENCE DESCRIPTION: SEQ ID NO:4:

Arg Met Ser Leu
1

(2) INFORMATION FOR SEQ ID NO:5:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Region
    (B) LOCATION: one-of(2)
    (D) OTHER INFORMATION: /note= "Xaa is norleucine."

(xi) SEQUENCE DESCRIPTION: SEQ ID NO:5:

Arg Xaa Ser Leu
1

(2) INFORMATION FOR SEQ ID NO:6:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

Gly Arg Ser Leu
1

(2) INFORMATION FOR SEQ ID NO:7:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

Leu Ala Leu Leu
1

(2) INFORMATION FOR SEQ ID NO:8:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

Leu Gly Ile Ala
1

(2) INFORMATION FOR SEQ ID NO:9:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:9:

Gln Gly Ile Leu
1

( 2 ) INFORMATION FOR SEQ ID NO:10:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:10:

Gln Gly Leu Leu
1

( 2 ) INFORMATION FOR SEQ ID NO:11:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:11:

Gln Gly Ile Ala
1

( 2 ) INFORMATION FOR SEQ ID NO:12:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:12:

Gln Ala Ile Ala
1

( 2 ) INFORMATION FOR SEQ ID NO:13:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:13:

Glu Gly Leu Arg
1

( 2 ) INFORMATION FOR SEQ ID NO:14:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

Gly His Phe Arg
1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Leu Glu Val Met
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(4)
        ( D ) OTHER INFORMATION: /note= "Xaa is norleucine."

( x i ) SEQUENCE DESCRIPTION: SEQ ID NO:16:

Leu Glu Val Xaa
1

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Ile His Ile Gln
1

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Ala Asn Tyr Asn ( 2 ) INFORMATION FOR SEQ ID NO:19:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Ala Gly Glu Arg
1

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Ala Gly Phe Ala
1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Gln Gly Leu Ala
1

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Ala Gln Phe Val
1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Ala Gly Val Glu ( 2 ) INFORMATION FOR SEQ ID NO:24:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Phe Cys Met Leu
1

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(3)
        ( D ) OTHER INFORMATION: /note= "Xaa is norleucine."

( x i ) SEQUENCE DESCRIPTION: SEQ ID NO:25:

Phe Cys Xaa Leu
1

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Asp Gly Ser Gly Gly Gly Glu Asp Glu Lys
1                       5                         10

( 2 ) INFORMATION FOR SEQ ID NO:27:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Lys Glu Asp Gly Gly Asp Lys
1                       5

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

Asp  Gly  Ser  Gly  Glu  Asp  Glu  Lys
1                      5

( 2 ) INFORMATION FOR SEQ ID NO:29:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:29:

Asp  Gly  Gly  Gly  Lys  Lys
1                      5

( 2 ) INFORMATION FOR SEQ ID NO:30:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:30:

Lys  Glu  Asp  Glu  Gly  Ser  Gly  Asp  Lys
1                      5

( 2 ) INFORMATION FOR SEQ ID NO:31:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Region
                ( B ) LOCATION: one-of(5)
                ( D ) OTHER INFORMATION: /note= "Xaa is norleucine."

( x i ) SEQUENCE DESCRIPTION: SEQ ID NO:31:

Asp  Ala  Ile  Pro  Xaa  Ser  Ile  Pro  Cys
1                      5

( 2 ) INFORMATION FOR SEQ ID NO:32:

( i ) SEQUENCE CHARACTERISTICS:
                ( A ) LENGTH: 5 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:32:

Ile  Pro  Met  Ser  Ile
1                      5

( 2 ) INFORMATION FOR SEQ ID NO:33:

( i ) SEQUENCE CHARACTERISTICS:

(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

Asp Ala Ile Pro Met Ser Ile Pro Cys
1               5

(2) INFORMATION FOR SEQ ID NO:34:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Lys Lys Gly Gly Gly
1               5

(2) INFORMATION FOR SEQ ID NO:35:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(5)
(D) OTHER INFORMATION: /note= "Xaa is Met or norleucine."

(ix) FEATURE:
(A) NAME/KEY: Region
(B) LOCATION: one-of(8)
(D) OTHER INFORMATION: /note= "Xaa is Pro or aminoisobutyric acid."

(xi) SEQUENCE DESCRIPTION: SEQ ID NO:35:

Asp Ala Ile Pro Xaa Ser Ile Xaa Cys
1               5

(2) INFORMATION FOR SEQ ID NO:36:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Met, aminoisobutryic aci or Pro."

(ix) FEATURE:
(A) NAME/KEY: Region
(B) LOCATION: one-of(3)
(D) OTHER INFORMATION: /note= "Xaa is Thr, aminoisobtyric acid or Pro."

(ix) FEATURE:
(A) NAME/KEY: Region (B) LOCATION: one-of(8)
(D) OTHER INFORMATION: /note= "Xaa is Pro or aminoisobutyric acid."

(x i) SEQUENCE DESCRIPTION: SEQ ID NO:36:

Asp Xaa Xaa Gly Arg Thr Gly Xaa Cys
1               5

(2) INFORMATION FOR SEQ ID NO:37:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Region
    (B) LOCATION: one-of(2)
    (D) OTHER INFORMATION: /note= "Xaa is Ala or aminoisobutyric acid."

(i x) FEATURE:
    (A) NAME/KEY: Region
    (B) LOCATION: one-of(3)
    (D) OTHER INFORMATION: /note= "Xaa is Thr, aminoisobutyric aci or Pro."

(i x) FEATURE:
    (A) NAME/KEY: Region
    (B) LOCATION: one-of(6)
    (D) OTHER INFORMATION: /note= "Xaa is Met or norleucine."

(i x) FEATURE:
    (A) NAME/KEY: Region
    (B) LOCATION: one-of(8)
    (D) OTHER INFORMATION: /note= "Xaa is Pro or aminoisobutyric acid."

(x i) SEQUENCE DESCRIPTION: SEQ ID NO:37:

Asp Xaa Xaa Phe Cys Xaa Leu Xaa Cys
1               5

(2) INFORMATION FOR SEQ ID NO:38:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Region
    (B) LOCATION: one-of(2)
    (D) OTHER INFORMATION: /note= "Xaa is aminoisobutyric acid."

(i x) FEATURE:
    (A) NAME/KEY: Region
    (B) LOCATION: one-of(3)
    (D) OTHER INFORMATION: /note= "Xaa is Ser, aminoisobutyric aci or Pro."

(i x) FEATURE:
    (A) NAME/KEY: Region
    (B) LOCATION: one-of(5)
    (D) OTHER INFORMATION: /note= "Xaa is Met or norleucine."

(i x) FEATURE:
    (A) NAME/KEY: Region
    (B) LOCATION: one-of(8)
    (D) OTHER INFORMATION: /note= "Xaa is Pro or aminoisobutyric acid."

( x i ) SEQUENCE DESCRIPTION: SEQ ID NO:38:

```
Asp  Xaa  Xaa  Arg  Xaa  Ser  Leu  Xaa  Cys
 1                  5
```

( 2 ) INFORMATION FOR SEQ ID NO:39:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(2)
        ( D ) OTHER INFORMATION: /note= "Xaa is aminoisobutyric
            acid."

( i x ) FEATURE:
        ( A ) NAME/KEY: Region
        ( B ) LOCATION: one-of(3)
        ( D ) OTHER INFORMATION: /note= "Xaa is Ala, aminoisobutyric aci
            or Pro."

( i x ) FEATURE:
        ( A ) NAME/KEY: Region
        ( B ) LOCATION: one-of(8)
        ( D ) OTHER INFORMATION: /note= "Xaa is Pro or aminoisobutyric
            acid."

( x i ) SEQUENCE DESCRIPTION: SEQ ID NO:39:

```
Asp  Xaa  Xaa  Gly  Arg  Ser  Leu  Xaa  Cys
 1                  5
```

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(2)
        ( D ) OTHER INFORMATION: /note= "Xaa is aminoisobutyric
            acid."

( i x ) FEATURE:
        ( A ) NAME/KEY: Region
        ( B ) LOCATION: one-of(3)
        ( D ) OTHER INFORMATION: /note= "Xaa is Thr, aminoisobutyric aci
            or Pro."

( i x ) FEATURE:
        ( A ) NAME/KEY: Region
        ( B ) LOCATION: one-of(8)
        ( D ) OTHER INFORMATION: /note= "Xaa is Pro or aminoisobutyric
            acid."

( x i ) SEQUENCE DESCRIPTION: SEQ ID NO:40:

```
Asp  Xaa  Xaa  Leu  Leu  Ser  Leu  Xaa  Cys
 1                  5
```

( 2 ) INFORMATION FOR SEQ ID NO:41:

( i ) SEQUENCE CHARACTERISTICS:
        ( A ) LENGTH: 9 amino acids (B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Gly or aminoisobutyric acid."

(ix) FEATURE:
(A) NAME/KEY: Region
(B) LOCATION: one-of(3)
(D) OTHER INFORMATION: /note= "Xaa is Pro or aminoisobutyric acid."

(ix) FEATURE:
(A) NAME/KEY: Region
(B) LOCATION: one-of(8)
(D) OTHER INFORMATION: /note= "Xaa is Pro or aminoisobutyric acid."

(xi) SEQUENCE DESCRIPTION: SEQ ID NO:41:

```
Asp Xaa Xaa Leu Gly Ile Ala Xaa Cys
1               5
```

(2) INFORMATION FOR SEQ ID NO:42:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Gly, aminoisobutyric acid or Pro."

(ix) FEATURE:
(A) NAME/KEY: Region
(B) LOCATION: one-of(3)
(D) OTHER INFORMATION: /note= "Xaa is Pro or aminoisobutyric acid."

(ix) FEATURE:
(A) NAME/KEY: Region
(B) LOCATION: one-of(8)
(D) OTHER INFORMATION: /note= "Xaa is Pro or aminoisobutyric acid."

(xi) SEQUENCE DESCRIPTION: SEQ ID NO:42:

```
Asp Xaa Xaa Gln Gly Ile Leu Xaa Cys
1               5
```

(2) INFORMATION FOR SEQ ID NO:43:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Gly, aminoisobutyric acid or Pro."

( i x ) FEATURE:
    ( A ) NAME/KEY: Region
    ( B ) LOCATION: one-of(3)
    ( D ) OTHER INFORMATION: /note= "Xaa is Pro or aminoisobutyric acid."

( i x ) FEATURE:
    ( A ) NAME/KEY: Region
    ( B ) LOCATION: one-of(8)
    ( D ) OTHER INFORMATION: /note= "Xaa is Pro or aminoisobutyric acid."

( x i ) SEQUENCE DESCRIPTION: SEQ ID NO:43:

```
Asp Xaa Xaa Gln Gly Leu Leu Xaa Cys
 1               5
```

( 2 ) INFORMATION FOR SEQ ID NO:44:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(2)
        ( D ) OTHER INFORMATION: /note= "Xaa is Gly, aminoisobutyric acid or Pro."

( i x ) FEATURE:
        ( A ) NAME/KEY: Region
        ( B ) LOCATION: one-of(3)
        ( D ) OTHER INFORMATION: /note= "Xaa is Pro or aminoisobutyric acid."

( i x ) FEATURE:
        ( A ) NAME/KEY: Region
        ( B ) LOCATION: one-of(8)
        ( D ) OTHER INFORMATION: /note= "Xaa is Pro or aminoisobutyric acid."

( x i ) SEQUENCE DESCRIPTION: SEQ ID NO:44:

```
Asp Xaa Xaa Gln Gly Ile Ala Xaa Cys
 1               5
```

( 2 ) INFORMATION FOR SEQ ID NO:45:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(2)
        ( D ) OTHER INFORMATION: /note= "Xaa is Gly, aminoisobutyric acid or Pro."

( i x ) FEATURE:
        ( A ) NAME/KEY: Region
        ( B ) LOCATION: one-of(3)
        ( D ) OTHER INFORMATION: /note= "Xaa is Pro or aminoisobutyric acid."

( i x ) FEATURE:
        ( A ) NAME/KEY: Region
        ( B ) LOCATION: one-of(8)
        ( D ) OTHER INFORMATION: /note= "Xaa is Pro or aminoisobutyric acid."

(xi) SEQUENCE DESCRIPTION: SEQ ID NO:45:

Asp Xaa Xaa Gln Ala Ile Ala Xaa Cys
1               5

(2) INFORMATION FOR SEQ ID NO:46:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(2)
        (D) OTHER INFORMATION: /note= "Xaa is Gly, aminoisobutyric acid or Pro."

(ix) FEATURE:
        (A) NAME/KEY: Region
        (B) LOCATION: one-of(3)
        (D) OTHER INFORMATION: /note= "Xaa is Pro or aminoisobutyric acid."

(ix) FEATURE:
        (A) NAME/KEY: Region
        (B) LOCATION: one-of(8)
        (D) OTHER INFORMATION: /note= "Xaa is Pro or aminoisobutyric acid."

(xi) SEQUENCE DESCRIPTION: SEQ ID NO:46:

Asp Xaa Xaa Glu Gly Leu Arg Xaa Cys
1               5

(2) INFORMATION FOR SEQ ID NO:47:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(2)
        (D) OTHER INFORMATION: /note= "Xaa is Asp, aminoisobutyric acid or Pro."

(ix) FEATURE:
        (A) NAME/KEY: Region
        (B) LOCATION: one-of(3)
        (D) OTHER INFORMATION: /note= "Xaa is Val, aminoisobutyric acid or Pro."

(ix) FEATURE:
        (A) NAME/KEY: Region
        (B) LOCATION: one-of(8)
        (D) OTHER INFORMATION: /note= "Xaa is Pro or aminoisobutyric acid."

(xi) SEQUENCE DESCRIPTION: SEQ ID NO:47:

Asp Xaa Xaa Gly His Phe Arg Xaa Cys
1               5

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS: single (D) TOPOLOGY: linear (i i) MOLECULE TYPE: peptide (i x) FEATURE:
    (A) NAME/KEY: Region
    (B) LOCATION: one-of(2)
    (D) OTHER INFORMATION: /note= "Xaa is Asp, aminoisobutyric acid or Pro."

(i x) FEATURE:
    (A) NAME/KEY: Region
    (B) LOCATION: one-of(3)
    (D) OTHER INFORMATION: /note= "Xaa is Thr, aminoisobutyric acid or Pro."

(i x) FEATURE:
    (A) NAME/KEY: Region
    (B) LOCATION: one-of(7)
    (D) OTHER INFORMATION: /note= "Xaa is Met or norleucine."

(i x) FEATURE:
    (A) NAME/KEY: Region
    (B) LOCATION: one-of(8)
    (D) OTHER INFORMATION: /note= "Xaa is Pro or aminoisobutyric acid."

(x i) SEQUENCE DESCRIPTION: SEQ ID NO:48:

Asp Xaa Xaa Leu Glu Val Xaa Xaa Cys
1               5

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Region
    (B) LOCATION: one-of(2)
    (D) OTHER INFORMATION: /note= "Xaa is Arg, aminoisobutyric acid or Pro."

(i x) FEATURE:
    (A) NAME/KEY: Region
    (B) LOCATION: one-of(3)
    (D) OTHER INFORMATION: /note= "Xaa is Ala, aminoisobutyric acid or Pro."

(i x) FEATURE:
    (A) NAME/KEY: Region
    (B) LOCATION: one-of(8)
    (D) OTHER INFORMATION: /note= "Xaa is Pro or aminoisobutyric acid."

(x i) SEQUENCE DESCRIPTION: SEQ ID NO:49:

Asp Xaa Xaa Ile His Ile Gln Xaa Cys
1               5

(2) INFORMATION FOR SEQ ID NO:50:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Region
    (B) LOCATION: one-of(2)

(D) OTHER INFORMATION: /note= "Xaa is Gly, aminoisobutyric acid or Pro."

(ix) FEATURE:
 (A) NAME/KEY: Region
 (B) LOCATION: one-of(3)
 (D) OTHER INFORMATION: /note= "Xaa is Pro or aminoisobutyric acid."

(ix) FEATURE:
 (A) NAME/KEY: Region
 (B) LOCATION: one-of(8)
 (D) OTHER INFORMATION: /note= "Xaa is Pro or aminoisobutyric acid."

(xi) SEQUENCE DESCRIPTION: SEQ ID NO:50:

Asp Xaa Xaa Ala Gly Glu Arg Xaa Cys
1               5

(2) INFORMATION FOR SEQ ID NO:51:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Region
  (B) LOCATION: one-of(2)
  (D) OTHER INFORMATION: /note= "Xaa is Gly, aminoisobutyric acid or Pro."

(ix) FEATURE:
  (A) NAME/KEY: Region
  (B) LOCATION: one-of(3)
  (D) OTHER INFORMATION: /note= "Xaa is Pro or aminoisobutyric acid."

(ix) FEATURE:
  (A) NAME/KEY: Region
  (B) LOCATION: one-of(8)
  (D) OTHER INFORMATION: /note= "Xaa is Pro or aminoisobutyric acid."

(xi) SEQUENCE DESCRIPTION: SEQ ID NO:51:

Asp Xaa Xaa Ala Gly Phe Ala Xaa Cys
1               5

(2) INFORMATION FOR SEQ ID NO:52:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Region
  (B) LOCATION: one-of(2)
  (D) OTHER INFORMATION: /note= "Xaa is Gly, aminoisobutyric acid or Pro."

(ix) FEATURE:
  (A) NAME/KEY: Region
  (B) LOCATION: one-of(3)
  (D) OTHER INFORMATION: /note= "Xaa is Pro or aminoisobutyric acid."

(ix) FEATURE:
  (A) NAME/KEY: Region
  (B) LOCATION: one-of(8)

(D) OTHER INFORMATION: /note= "Xaa is Pro or aminoisobutyric acid."

(xi) SEQUENCE DESCRIPTION: SEQ ID NO:52:

Asp Xaa Xaa Gln Gly Leu Ala Xaa Cys
1               5

(2) INFORMATION FOR SEQ ID NO:53:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(2)
        (D) OTHER INFORMATION: /note= "Xaa is Asp, aminoisobutyric acid or Pro."

(ix) FEATURE:
        (A) NAME/KEY: Region
        (B) LOCATION: one-of(3)
        (D) OTHER INFORMATION: /note= "Xaa is Val, aminoisobutyric acid or Pro."

(ix) FEATURE:
        (A) NAME/KEY: Region
        (B) LOCATION: one-of(8)
        (D) OTHER INFORMATION: /note= "Xaa is Pro or aminoisobutyric acid."

(xi) SEQUENCE DESCRIPTION: SEQ ID NO:53:

Asp Xaa Xaa Ala Gln Phe Val Xaa Cys
1               5

(2) INFORMATION FOR SEQ ID NO:54:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(2)
        (D) OTHER INFORMATION: /note= "Xaa is Gly, aminoisobutyric acid or Pro."

(ix) FEATURE:
        (A) NAME/KEY: Region
        (B) LOCATION: one-of(3)
        (D) OTHER INFORMATION: /note= "Xaa is Asp or aminoisobutyric acid."

(ix) FEATURE:
        (A) NAME/KEY: Region
        (B) LOCATION: one-of(8)
        (D) OTHER INFORMATION: /note= "Xaa is Pro or aminoisobutyric acid."

(xi) SEQUENCE DESCRIPTION: SEQ ID NO:54:

Asp Xaa Xaa Ala Gly Val Gln Xaa Cys
1               5

(2) INFORMATION FOR SEQ ID NO:55:

(i) SEQUENCE CHARACTERISTICS:
        (A) LENGTH: 9 amino acids (B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Gly, aminoisobutyric acid or Pro."

(ix) FEATURE:
(A) NAME/KEY: Region
(B) LOCATION: one-of(3)
(D) OTHER INFORMATION: /note= "Xaa is Pro or aminoisobutyric acid."

(ix) FEATURE:
(A) NAME/KEY: Region
(B) LOCATION: one-of(8)
(D) OTHER INFORMATION: /note= "Xaa is Pro or aminoisobutyric acid."

(xi) SEQUENCE DESCRIPTION: SEQ ID NO:55:

Asp Xaa Xaa Gln Gly Ile Ala Xaa Cys
1               5

(2) INFORMATION FOR SEQ ID NO:56:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Asp, aminoisobutyric acid or Pro."

(ix) FEATURE:
(A) NAME/KEY: Region
(B) LOCATION: one-of(3)
(D) OTHER INFORMATION: /note= "Xaa is Val, aminoisobutyric acid or Pro."

(ix) FEATURE:
(A) NAME/KEY: Region
(B) LOCATION: one-of(8)
(D) OTHER INFORMATION: /note= "Xaa is Pro or aminoisobutyric acid."

(xi) SEQUENCE DESCRIPTION: SEQ ID NO:56:

Asp Xaa Xaa Ala Asn Tyr Asn Xaa Cys
1               5